United States Patent
Milo et al.

(10) Patent No.: US 10,294,482 B2
(45) Date of Patent: May 21, 2019

(54) RECOMBINANT MICROORGANISMS CAPABLE OF CARBON FIXATION

(71) Applicant: Yeda Research and Development Co. Ltd., Rehovot (IL)

(72) Inventors: Ron Milo, Kfar-Saba (IL); Niv Antonovsky, Rehovot (IL); Elad Noor, Rehovot (IL); Arren Bar-Even, Rehovot (IL); Yehudit Zohar, Rehovot (IL); Lior Zelcbuch, Rehovot (IL); Shmuel Gleizer, Rehovot (IL); Shira Amram, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 80 days.

(21) Appl. No.: 15/312,734

(22) PCT Filed: May 21, 2015

(86) PCT No.: PCT/IL2015/050540
§ 371 (c)(1),
(2) Date: Nov. 21, 2016

(87) PCT Pub. No.: WO2015/177800
PCT Pub. Date: Nov. 26, 2015

(65) Prior Publication Data
US 2017/0183665 A1    Jun. 29, 2017

Related U.S. Application Data

(60) Provisional application No. 62/001,736, filed on May 22, 2014.

(51) Int. Cl.
| | | |
|---|---|---|
| *C12N 15/70* | (2006.01) | |
| *C12N 15/52* | (2006.01) | |
| *C12N 15/74* | (2006.01) | |
| *C07K 14/195* | (2006.01) | |
| *C07K 14/245* | (2006.01) | |
| *C12N 1/20* | (2006.01) | |
| *C12N 9/04* | (2006.01) | |
| *C12N 9/10* | (2006.01) | |
| *C12N 9/12* | (2006.01) | |
| *C12N 9/88* | (2006.01) | |
| *C12N 9/90* | (2006.01) | |

(52) U.S. Cl.
CPC ............ *C12N 15/70* (2013.01); *C07K 14/195* (2013.01); *C07K 14/245* (2013.01); *C12N 1/20* (2013.01); *C12N 9/0006* (2013.01); *C12N 9/1025* (2013.01); *C12N 9/1205* (2013.01); *C12N 9/88* (2013.01); *C12N 9/90* (2013.01); *C12Y 101/01049* (2013.01); *C12Y 203/03009* (2013.01); *C12Y 207/01011* (2013.01); *C12Y 207/01019* (2013.01); *C12Y 401/01039* (2013.01); *C12Y 402/01011* (2013.01); *C12Y 504/02* (2013.01)

(58) Field of Classification Search
None
See application file for complete search history.

(56) References Cited

FOREIGN PATENT DOCUMENTS

| WO | WO 2009/036095 | * 3/2009 | ........... C07K 14/195 |
|---|---|---|---|
| WO | WO 2011/099006 | 8/2011 | |
| WO | WO 2015/177800 | 11/2015 | |

OTHER PUBLICATIONS

Raines et al., Transgenic approaches to manipulate the environmental responses of the C3 carbon fixation cycle, Plant, Cell and Environment, (2006), 29.*
Tick et al., Carbon Fixation, Chapter—Towards Engineered Light—Energy Conversion in Nonphotosynthetic Microorganisms, Synthetic Biology, Tools and Applications, Dec. 2013, pp. 303-316.*
Communication Relating to the Results of the Partial International Search dated Oct. 22, 2015 From the International Searching Authority Re. Application No. PCT/IL2015/050540.
International Preliminary Report on Patentability dated Dec. 1, 2016 From the International Bureau of WIPO Re. Application No. PCT/IL2015/050540. (10 Pages)
International Search Report and the Written Opinion dated Jan. 29, 2016 From the International Searching Authority Re. Application No. PCT/IL2015/050540.
Communication Pursuant to Article 94(3) EPC dated Feb. 15, 2018 From the European Patent Office Re. Application No. 15753495.9. (3 Pages)

* cited by examiner

*Primary Examiner* — Channing S Mahatan

(57) ABSTRACT

A microorganism which is genetically modified so that it produces a first essential biomass precursor by metabolizing $CO_2$ using a recombinant carbon fixation enzyme is disclosed. The microorganism produces a second biomass precursor by metabolizing an organic carbon source and not by metabolizing $CO_2$. The microorganism does not use the organic carbon source for producing the first essential biomass precursor.

16 Claims, 19 Drawing Sheets
(14 of 19 Drawing Sheet(s) Filed in Color)
Specification includes a Sequence Listing.

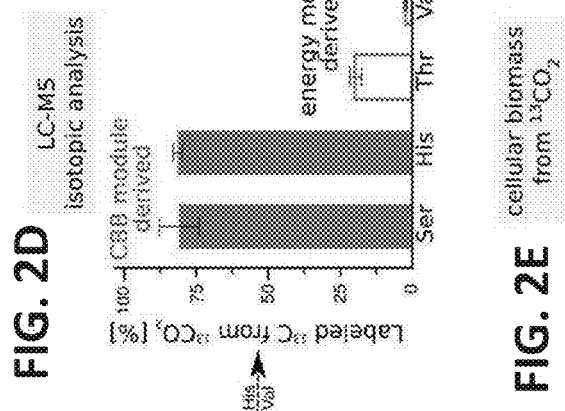
FIG. 2A RuBisCO dependent heterotroph ancestor
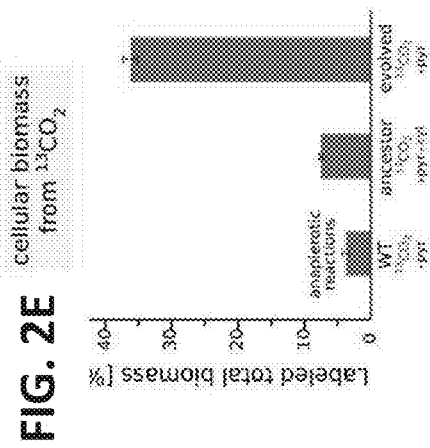
FIG. 2D LC-MS isotopic analysis
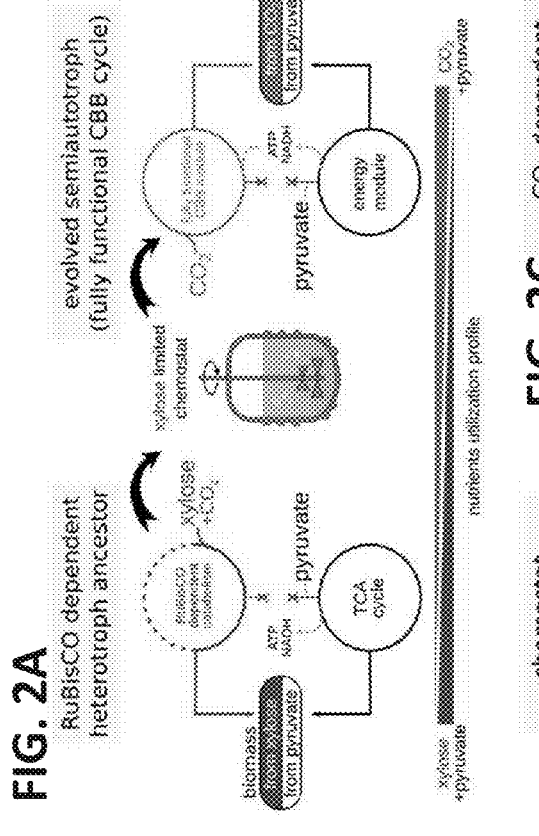
FIG. 2B chemostat evolution dynamics
FIG. 2C $CO_2$ dependent semiautotrophic growth
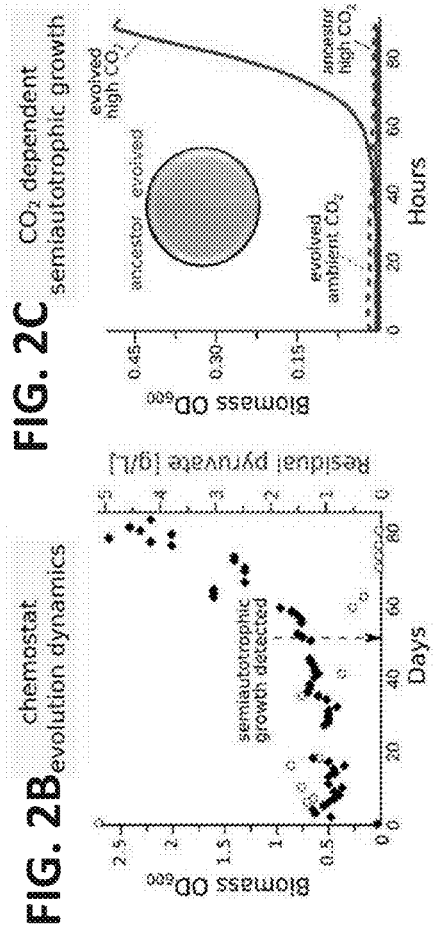
FIG. 2E cellular biomass from $^{13}CO_2$

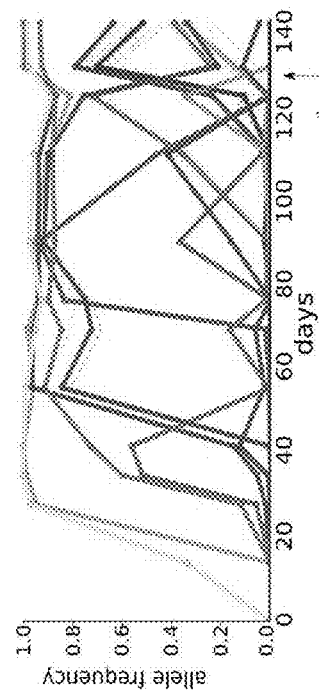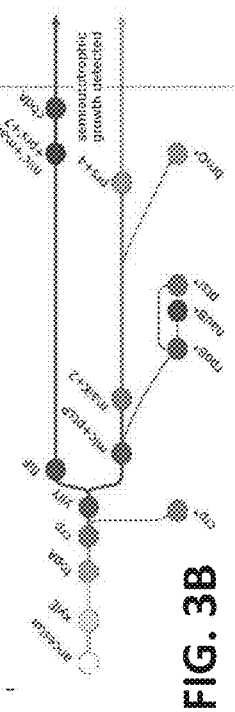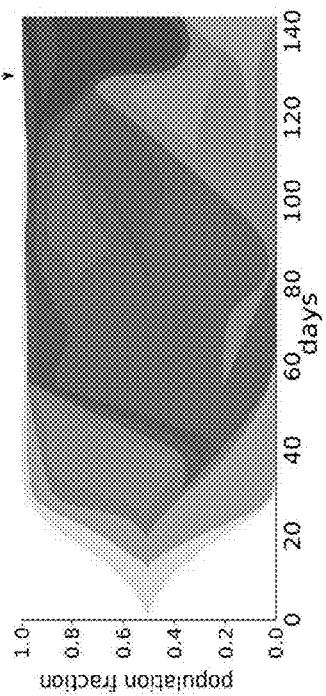
FIG. 3A
FIG. 3B

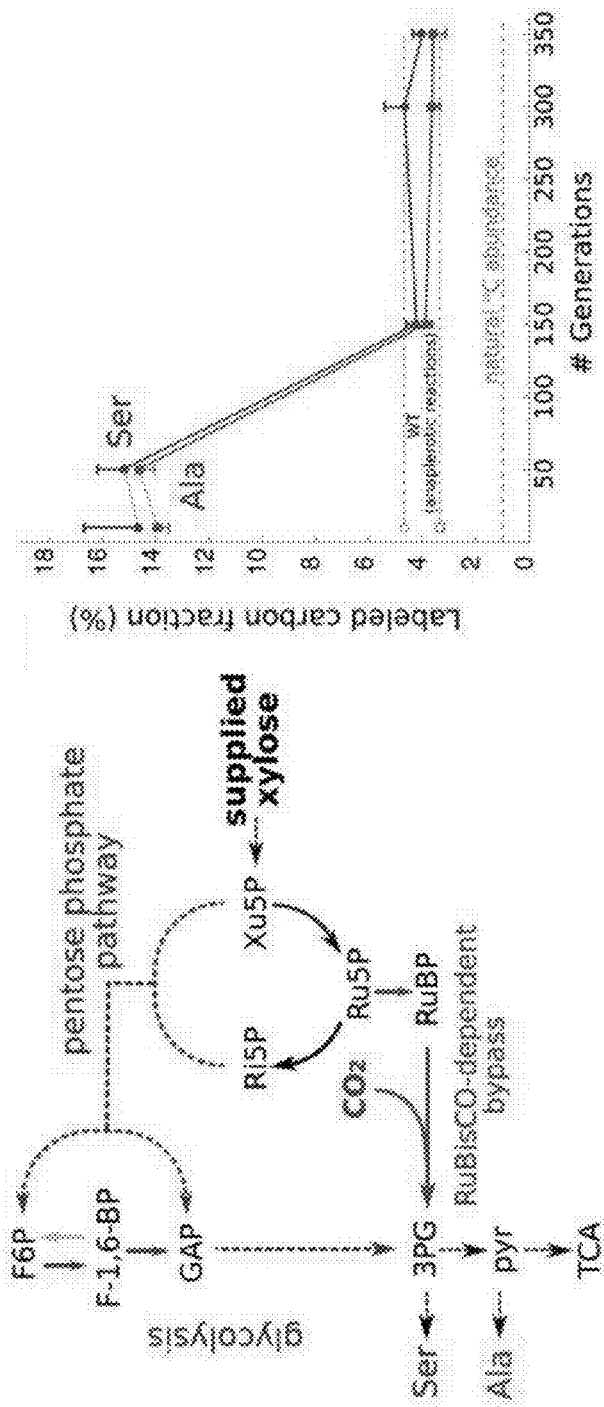

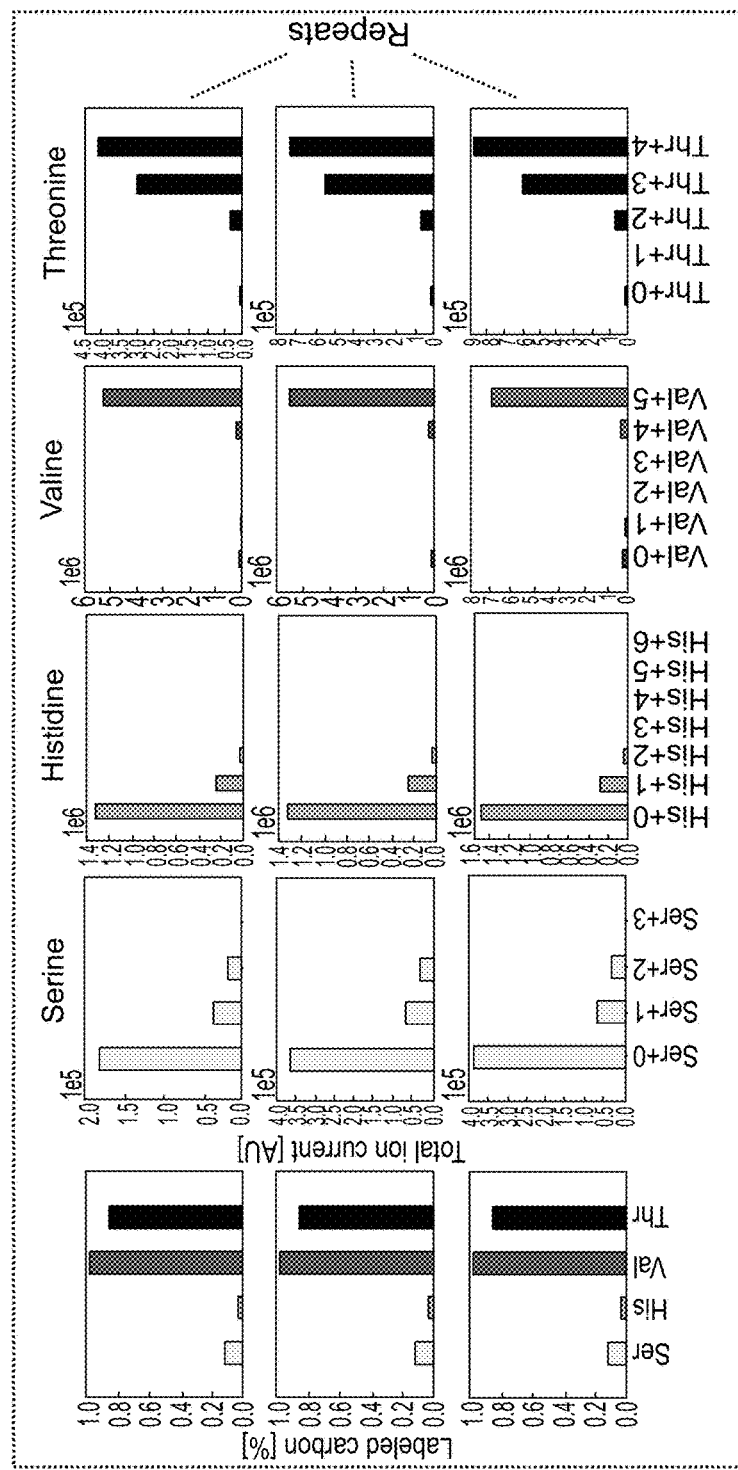

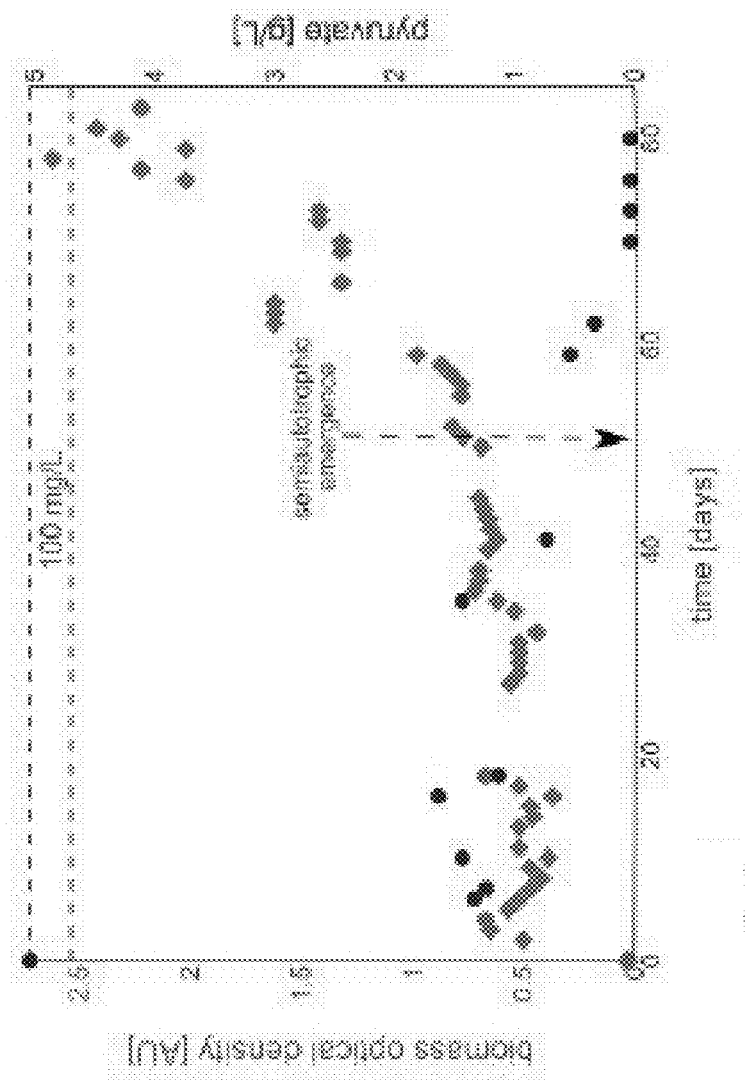

RECOMBINANT MICROORGANISMS CAPABLE OF CARBON FIXATION

RELATED APPLICATIONS

This application is a National Phase of PCT Patent Application No. PCT/IL2015/050540 having International filing date of May 21, 2015, which claims the benefit of priority under 35 USC § 119(e) of U.S. Provisional Patent Application No. 62/001,736 filed on May 22, 2014. The contents of the above applications are all incorporated by reference as if fully set forth herein in their entirety.

SEQUENCE LISTING STATEMENT

The ASCII file, entitled 67719SequenceListing.txt, created on Nov. 21, 2016, comprising 17,416 bytes, submitted concurrently with the filing of this application is incorporated herein by reference.

FIELD AND BACKGROUND OF THE INVENTION

The present invention, in some embodiments thereof, relates to recombinant non-autotrophic microorganisms that are capable of carbon fixation.

Carbon fixation plays an essential role in ecosystems by providing a continuous flux of organic carbon into the biosphere. From a human perspective, the process of $CO_2$ assimilation dominates humanity's usage of land and water. Importantly, under human cultivation, where water, light and nutrients are abundant, carbon fixation often limits plant growth. Therefore, increasing the rate of carbon fixation is of major importance in the path towards agricultural and energetic sustainability.

Carbon fixation in plants, algae, cyanobacteria and many other bacterial lineages is achieved by the Calvin-Benson-Bassham (CBB) Cycle. The productivity of the CBB cycle is limited, under many conditions, by the relatively slow rate and lack of substrate specificity of the carboxylating enzyme RuBisCO. Previous attempts to utilize classic molecular biology tools to improve the rate and specificity of RuBisCO have achieved only limited success. Moreover, several lines of evidence indicate that in spite of its shortcomings, RuBisCO is already naturally optimized given the natural tradeoff between the enzyme's rate and specificity. Other enzymes of the CBB also were shown to constrain carbon fixation in certain circumstances. For example, tobacco plants overexpressing sedoheptulose-1,7-bisphosphatase were characterized by an increased photosynthetic rate and a 30% enhancement in biomass yield. Therefore, improving the rate of the CBB cycle seems to be quite a complex task that has many possible leads. Such a challenge can benefit significantly from the utilization of novel selection systems that can go far beyond the sequence divergence presented in plants.

WO 2011/099006 teaches plants and bacterial cells which are genetically modified so as to express enzymes of alternative (RuBisCO-independent) pathways in order to promote carbon fixation. Autotrophic *E. Coli* cells which express phosphoribulokinase and Ribulose-Bisphosphate Carboxylase are also disclosed.

SUMMARY OF THE INVENTION

According to an aspect of some embodiments of the present invention there is provided a microorganism which is genetically modified so that it produces a first essential biomass precursor by metabolizing $CO_2$ using a recombinant carbon fixation enzyme, wherein the microorganism produces a second biomass precursor by metabolizing an organic carbon source and not by metabolizing $CO_2$, wherein the microorganism does not use the organic carbon source for producing the first essential biomass precursor.

According to an aspect of some embodiments of the present invention there is provided a genetically modified *E. Coli* which expresses a recombinant phosphoribulokinase (prk) and Ribulose-Bisphosphate Carboxylase (RuBisCo) and has deletions in the genes zwf, pfkA and pfkB.

According to an aspect of some embodiments of the present invention there is provided cell culture comprising genetically modified *E. Coli* as described herein and a medium comprising acetate as an organic carbon source.

According to an aspect of some embodiments of the present invention there is provided a cell culture comprising the microorganism as described herein and a medium comprising the organic carbon source.

According to an aspect of some embodiments of the present invention there is provided a cell culture comprising the genetically modified *E. Coli* as described herein and a medium comprising an organic carbon source selected from the group consisting of pyruvate, malate, succinate, fumarate, oxaloacetate and citrate.

According to an aspect of some embodiments of the present invention there is provided a method of selecting a carbon fixation enzyme which is capable of altering the efficiency of carbon fixation in a plant comprising propagating the microorganism or *E. Coli* as described herein, wherein the recombinant carbon fixation enzyme is the carbon fixation enzyme and analyzing the efficiency of carbon fixation in the microorganism or *E. Coli*, wherein an increase or a decrease in efficiency of carbon fixation is indicative of a carbon fixation enzyme which is capable of altering the efficiency of carbon fixation in a plant.

According to an aspect of some embodiments of the present invention there is provided a plant comprising a heterologous carbon fixation enzyme, the plant having a higher efficiency of carbon fixation that the native plant.

According to an aspect of some embodiments of the present invention there is provided a method of propagating the microorganism or *E. Coli* as described herein comprising culturing the microorganism or *E. Coli* in a medium comprising an organic carbon source and an inorganic carbon source, thereby propagating the microorganism.

According to an aspect of some embodiments of the present invention there is provided a method of producing a chemical comprising culturing the microorganism or *E. Coli* as described herein in a medium comprising an organic carbon source and an inorganic carbon source and harvesting the chemical.

According to an aspect of some embodiments of the present invention there is provided a method of generating the microorganism described herein, the method comprising expressing in the *E. Coli* phosphoribulokinase (prk) and Ribulose-Bisphosphate Carboxylase (RuBisCo) and deleting in the *E. Coli* each of the genes zwf, pfkA and pfkB, thereby generating the microorganism.

According to some embodiments of the invention, the microorganism generates ATP and a reducing power by metabolizing the organic carbon source.

According to some embodiments of the invention, the first essential biomass precursor is derived solely from $CO_2$.

According to some embodiments of the invention, the first essential biomass precursor is derived from $CO_2$ and a second organic carbon source.

According to some embodiments of the invention, the microorganism is a bacteria or a yeast.

According to some embodiments of the invention, the yeast comprises S. cerevisiae.

According to some embodiments of the invention, the bacteria is an E. Coli.

According to some embodiments of the invention, the microorganism is not, in its native state, capable of biosynthesizing metabolites by utilizing $CO_2$ solely as a carbon source.

According to some embodiments of the invention, the microorganism is not a cyanobacteria.

According to some embodiments of the invention, the first essential biomass precursor is selected from the group consisting of 5-phospho-D-ribose α-1-pyrophosphate (PRPP), glucose-6P, fructose-6P, erythrose-4P, 3phophoglycerate and glycerol-3-phosphate.

According to some embodiments of the invention, the organic carbon source is selected from the group consisting of a pentose, a hexose and an organic acid.

According to some embodiments of the invention, the second organic carbon source is selected from the group consisting of a pentose, a hexose and an organic acid.

According to some embodiments of the invention, the organic acid is pyruvate.

According to some embodiments of the invention, the first organic carbon source is pyruvate and the second organic carbon source is xylose.

According to some embodiments of the invention, the recombinant carbon fixation enzyme is an enzyme of the Calvin Cycle.

According to some embodiments of the invention, when the microorganism is an E. Coli, the at least one enzyme of the Calvin Cycle comprises phosphoribulokinase (prk) and Ribulose-Bisphosphate Carboxylase (RuBisCo).

According to some embodiments of the invention, the E. Coli is further modified so as to down-regulate expression or activity of phosphofructokinase (pfk) or ribose-5-phosphate isomerase (rpi).

According to some embodiments of the invention, the E. Coli is further modified so as to down-regulate expression or activity of phosphoglycerate mutase (gpm).

According to some embodiments of the invention, the E. Coli has a deletion in a gene selected from the group consisting of glucose 6-phosphate-1-dehydrogenase (zwf) 6-phosphogluconate dehydratase (edd) and ketohydroxyglutarate aldolase (eda), malte synthase A (aceB), isocitrate lyase (aceA) and isocitrate dehydrogenase kinase/phosphatase (aceK).

According to some embodiments of the invention, the organic carbon source is selected from the group consisting of acetate, pyruvate, xylose, malate, succinate, fumarate, oxaloacetate and citrate.

According to some embodiments of the invention, the genetically modified E. Coli is an autotroph.

According to some embodiments of the invention, the genetically modified E. Coli has a deletion in gpmA and gpmB.

According to some embodiments of the invention, the genetically modified E. Coli has a deletion in aceBAK.

According to some embodiments of the invention, the genetically modified E. Coli has a deletion in aceBAK and malate synthase G (glcB).

According to some embodiments of the invention, the genetically modified E. Coli further has deletions in aceBAK, malate synthase G (glcB), phosphoenolpyruvate synthase (pps) and phosphoenolpyruvate carboxykinase (pck).

According to some embodiments of the invention, the genetically modified E. Coli further has deletions in aceBAK and phosphopyruvate hydratase (eno).

According to some embodiments of the invention, the genetically modified E. Coli has a deletion in at least one gene selected from the group consisting of prs, yciV, topA, ydgC, slyA, dcm, malQ, brnQ, ppsR, truB, xylE and trmA.

According to some embodiments of the invention, the genetically modified E. Coli has at least one mutation as set forth in Tables 2-6.

According to some embodiments of the invention, the cell culture comprises xylose as an additional organic carbon source.

According to some embodiments of the invention, the medium further comprises $CO_2$ at saturating levels.

According to some embodiments of the invention, the microorganism or E. Coli is immobilized on a solid support.

According to some embodiments of the invention, the medium comprises a single organic carbon source.

According to some embodiments of the invention, the medium comprises two organic carbon sources.

According to some embodiments of the invention, the culturing comprises altering the ratio of the two organic carbon sources in the medium.

According to some embodiments of the invention, the method further comprises expressing in the E. Coli carbonate dehydratase.

According to some embodiments of the invention, the method further comprises deleting the genes gpmA and gpmB in the E. Coli.

According to some embodiments of the invention, the method further comprises deleting the aceBAK in the E. Coli.

According to some embodiments of the invention, the method further comprises:

(a) performing random mutagenesis on the E. Coli; and (b) culturing the E. Coli under conditions that favor selection of a semi-autotrophic E. Coli.

According to some embodiments of the invention, the genome of the E. Coli is randomly mutated.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
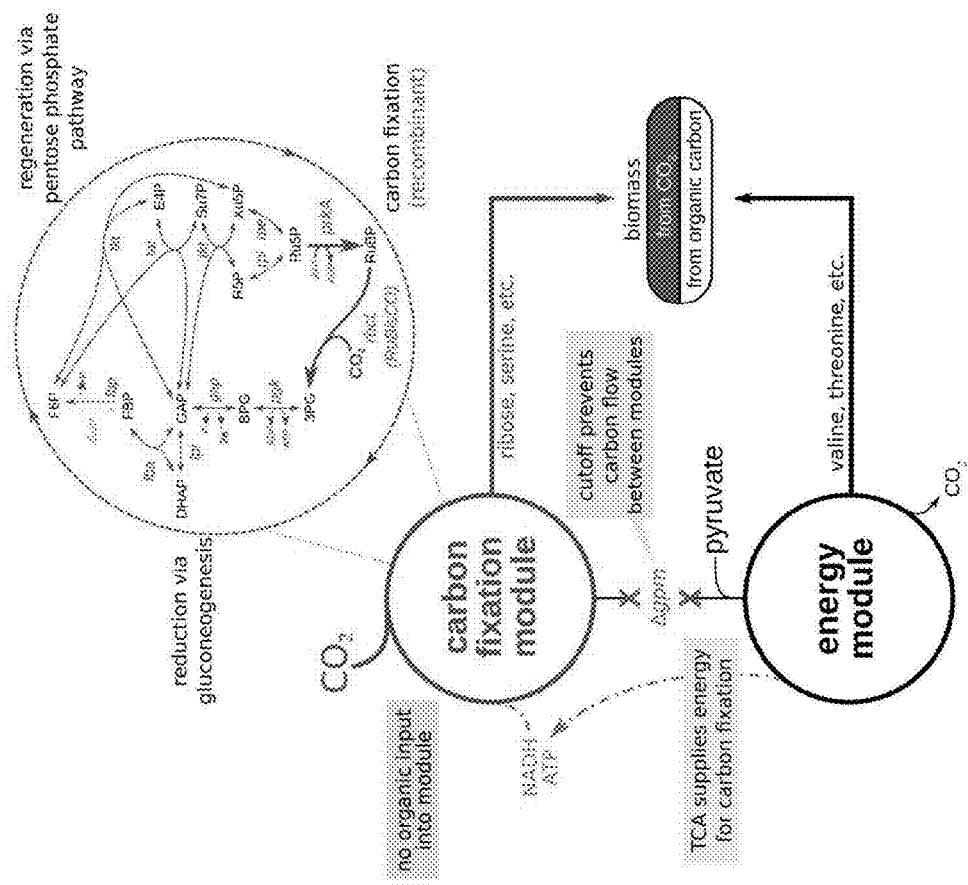

FIG. 1 is a diagram illustrating how decoupling energy production and carbon fixation in *E. Coli* achieves semiautotrophic growth. In native autotrophs, the CBB cycle enables the transformation of inorganic carbon and chemical energy into biomass precursors. Two recombinant enzymes are needed to complete the carbon fixation cycle in *E. Coli*: RuBisCO, the carboxylating enzyme, and the kinase prk. The remaining reactions required for the reduction and substrate regeneration phases of the cycle are endogenous to the metabolic network of the host, as part of the gluconeogenic and the pentose phosphate pathways. The deletion of the phosphoglycerate mutase genes (gpmA and gpmM) disrupts carbon flow in the glycolytic/gluconeogenic backbone and generates two disconnected sub-networks: (1) a carbon fixation module containing upper glycolysis, the pentose phosphate pathway and the two foreign CBB enzymes; (2) an energy-module, containing lower glycolysis and the TCA cycle supplying reducing power and ATP. In a scenario where an organic carbon source (e.g., pyruvate) is utilized by the energy module to supply the energetic demands of the cycle, the cellular building blocks derived from CBB-module metabolites (e.g., serine, pentose phosphates etc.) are synthesized from inorganic carbon using the non-native CBB pathway. The remainder of the biomass building blocks (those emanating from the energy module metabolites. e.g., valine, threonine) as well as the energy requirements of the cell, are supplied via the catabolism of the organic carbon source. In such a semiautotrophic growth mode, $CO_2$ and energy carriers are the sole inputs for the production of biomass precursors using the CBB cycle.

Figure 8:
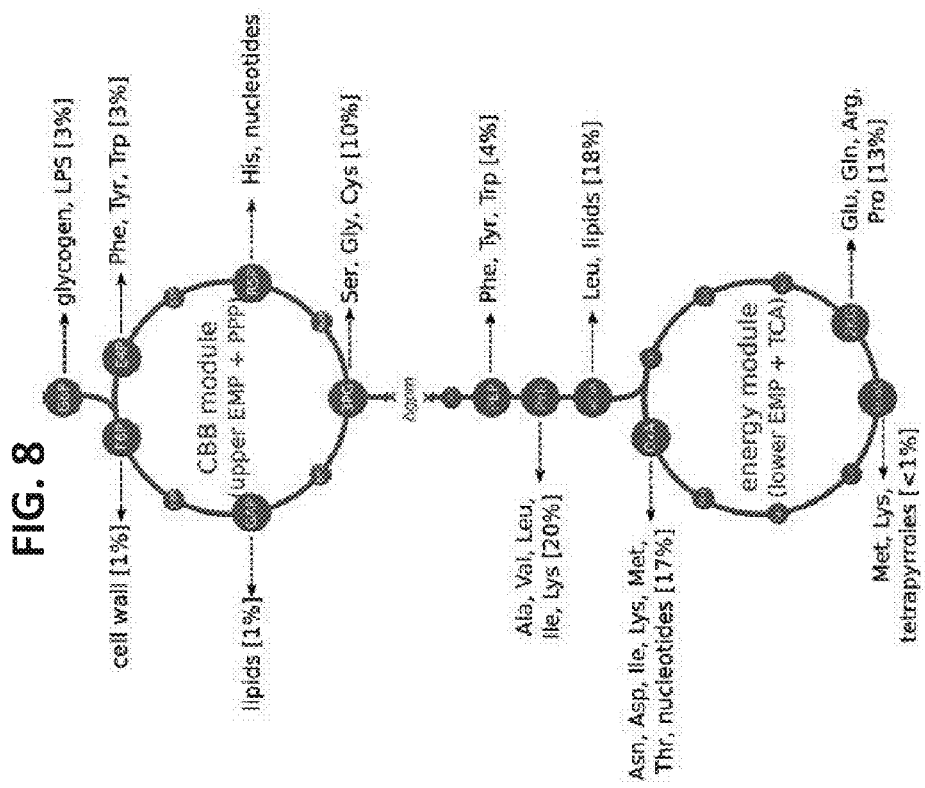
Figure 10A:
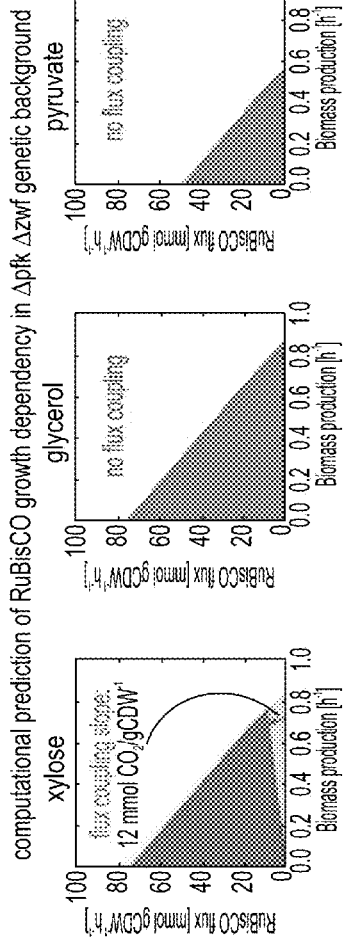
Figure 10B:
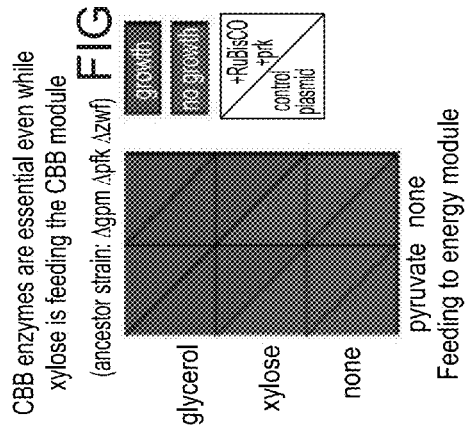
Figure 10C:
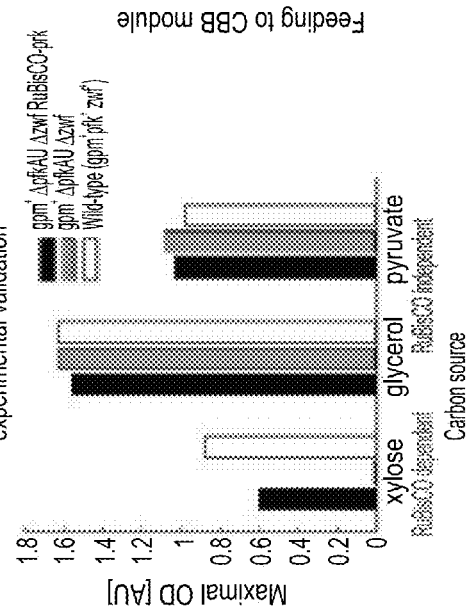

FIGS. 2A-E illustrate how chemostat evolution leads to a semiautotrophic phenotype. (a) Ancestor strain (left), containing gpmA and gpmM deletions was evolved in a xylose limited chemostat supplied with an excess of pyruvate and $CO_2$. Additional deletions of pfkA and pfkB and zwf results in RuBiSCO dependent (but not semiautotrophic) catabolism of xylose in the initial heterotrophic growth (FIGS. 10A-C). Propogation in a chemostat ensures that the xylose limited growth will result in a strong selective pressure towards achieving flux through the carbon fixation cycle. When mutations arise that create a fully functioning CBB cycle, they enable $CO_2$ to be the sole carbon input for the required biomass precursors. Xylose dependency is alleviated, allowing the semiautotrophic strain (right) to take over the population. (b) Around day 50 (arrow) an increase in OD and a decrease in pyruvate concentration (blue) was observed, indicating a takeover by an evolved clone. (c) In contrast to the ancestor strain, clones isolated from day 50 onwards were able to form colonies on agar plates supplemented with only pyruvate and requiring high $CO_2$ atmosphere. Evolved clones grew on pyruvate and $CO_2$ in liquid minimal media with a doubling time of ≈6 hours. (d) Isotopic labeling analysis, in which evolved clones were grown with isotopically labeled $^{13}CO_2$ and non-labeled pyruvate as an energy source, showed that biomass components synthesized from CBB module metabolites are almost fully labeled while biomass components originating from the energy module show low levels of labeling, as expected due to glycolytic cutoff, if the semiautotrophic growth mode is achieved. This indicates that the evolved strain is able to synthesize CBB module biomass precursors from $CO_2$ using the non-native CBB cycle, while the biomass precursors originating from the energy module are synthesized from the supplemented pyruvate. Note that threonine (Thr) is produced via an anaplerotic reaction that incorporates labeled inorganic carbon and thus the partial labeling observed was expected. (e) Isotopic carbon composition of total cell biomass was measured using an elemental mass analyzer. In the evolved semiautotrophic strain grown in labeled $^{13}CO_2$ atmosphere, over one third of cellular carbon originated from fixed inorganic carbon; this result is in line with the expected fraction of biomass precursors originating from the CBB module in the literature and corresponds to the fraction of biomass precursors produced from xylose in the ancestor strain under heterotrophic conditions (FIG. 8). Labeling of carbon atoms in the ancestor strain grown with non-labeled xylose is due to the RuBisCO dependent catabolism of pentoses (FIGS. 10A-C) and labeled carbon assimilation via anaplerotic reactions.

FIGS. 3A-B illustrate the dynamics of sequence evolution towards a semiautotrophic phenotype. (A) Temporal trajectories of mutations present in the evolving chemostat population. Single mutations and the average of mutation cohorts are plotted with a bold line; members of each cohort are dashed with matching color. The time at which semiautotrophic clones were first isolated from chemostat culture is marked with a dotted black line. Mutations that attained a frequency of at least 20% of the population are shown. Cell density and carbon source concentrations throughout the experiment are detailed in FIG. 11B (B) A lineage tree of mutations in the population and a Muller diagram depicting the population dynamics as inferred from the temporal trajectories of mutations appearing in (A). Four rapid sweeps by mutations appear in the first 30 days (blue sectors) followed by a bifurcation into two subpopulation, the green and the purple lineage, each of which led to a semiautotrophic phenotype. Mutations marked with a star appeared in a subpopulation but were overtaken by clonal interference. Detailed description of each mutation is given in Tables 2-6 in the Examples section below, including few large chromosomal events that were identified in isolated clones but could not be quantified accurately by sequencing a whole chemostat heterogeneous population and do not appear in the figure.

Figure 4B:
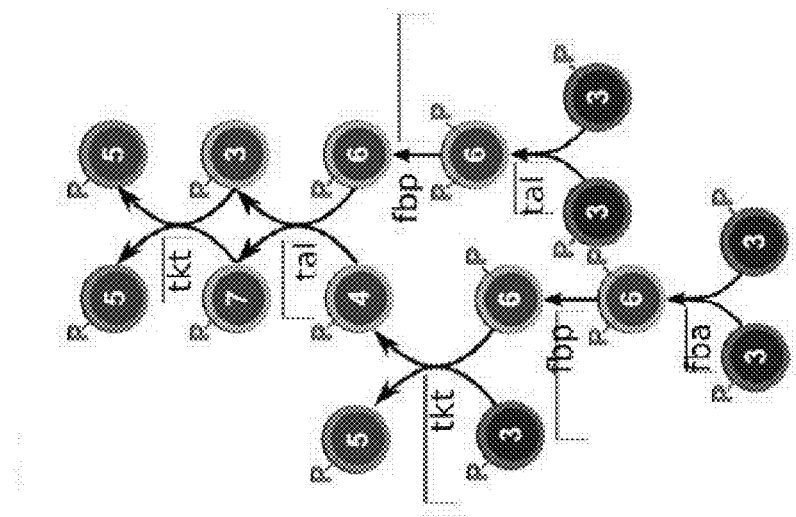
Figure 4A:
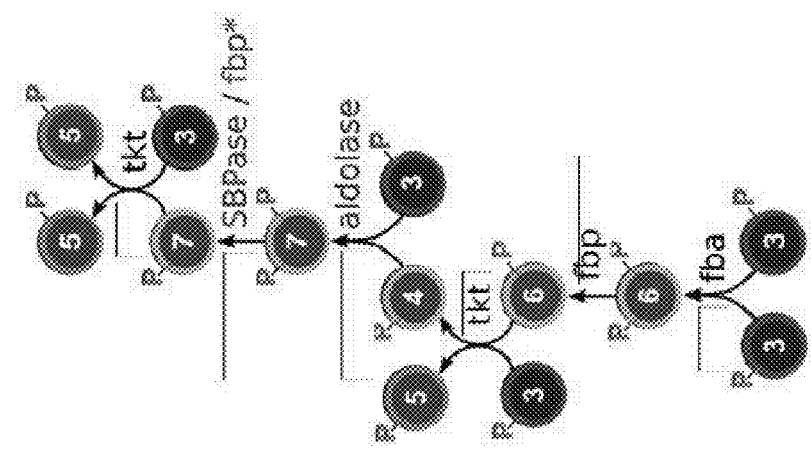
Figure 6A:
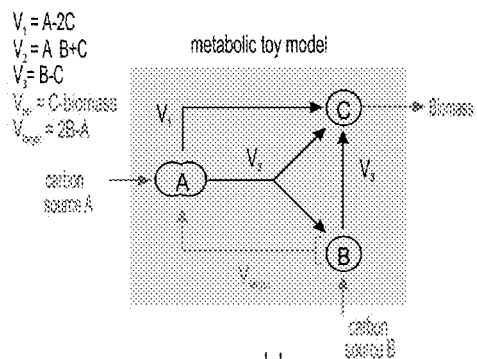
Figure 6B:
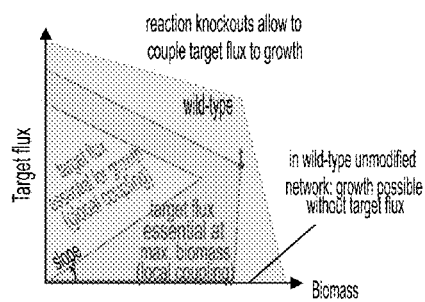
Figure 6C:
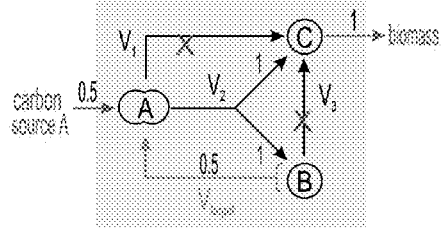
Figure 6D:
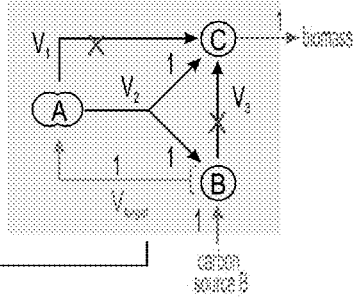
Figure 6E:
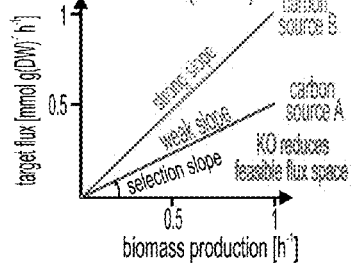
Figure 6F:
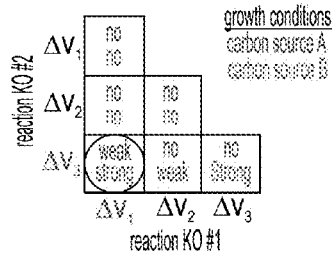

FIGS. 4A-B illustrate that endogenous Pentose Phosphate Pathway (PPP) enzymes of *E. coli* can regenerate pentoses in a nonnative Calvin cycle. (A) Pentose regeneration in the Calvin cycle takes in most photosynthetic organisms by utilizing an aldolase and a designated Sedoheptulose-bisphosphate phosphatase (SBPase) to dephosphorylate Sedoheptulose-bisphosphate (SBP). Alternatively, pentose regeneration can occur using a bifunctional FBPase (fbp*) as was found to be the case in cyanobacteria. (B) While the *E. coli* genome does not contain bona fide SBPase, RuBP regeneration can be accomplished in SBP-independent manner using the native enzymes of the PPP.

FIGS. 5A-B illustrate the loss of carbon fixation in a host expressing RuBisCO and prk on a background of an unperturbed metabolic network. (A) Schematic representation of two possible flux modes for pentose catabolism in recombinant *E. Coli* expressing RuBisCO and prk: native route via the pentosephosphate pathway (purple), and a RuBisCO dependent bypass from Ru5P to 3PG. While flux through the RuBisCO dependent branch is stoichiometrically feasible, it is not essential for growth due to the presence of the native route. (B) In vivo inorganic carbon assimilation was measured by incubating cells in M9 minimal media supplemented with unlabeled xylose (0.2%) and isotopically labeled $^{13}CO2$. Assimilation of $CO_2$ into biomass was quantified using mass spectrometry of aminoacid isotopomers from protein hydrolysate sampled during growth. Upon expression of recombinant CBB enzymes, almost a sixth of the carbons composing the intracellular 3PG pool are labeled (indicated by the labeling of serine in blue and alanine in red), indicating significant flux through the RuBisCO dependent branch. However, after ~100 generations in exponential growth a loss of carbon fixation activity is observed, presumably due to counter selection and takeover of clones in which recombinant expression has been diminished. Labeling in wildtype (WT) sample (without the RuBisCOprk encoding plasmid, dashed) beyond the expected natural fraction of $^{13}C$ in the supplied xylose (gray) is due to the anaplerotic reactions of the TCA cycle.

FIGS. 6A-F illustrate the systematic identification of metabolic configurations in which pathway activity is coupled to cellular growth. (A) Metabolic toy model containing three endogenous reactions (V1-V3) and one target recombinant reaction (Va). Flux through the target reaction is not essential for biomass generation on either of two considered carbon sources. (B) While frameworks for identifying gene deletion leading to the overproduction of a prespecified metabolite (such as OptKnock) ensure maximal flux through the target pathway at the point of maximal biomass production, maximal biomass production may not be the prevailing growth condition. Therefore, these frameworks do not ensure a global coupling between target flux and biomass production and therefore they do not make the target reaction essential for growth. The present inventors performed an exhaustive search for combinations of reaction knockouts in which $V_{target}$ is essential for growth when metabolizing a specific carbon source. (c) For example, eliminating reactions V1 and V3 results in making $V_{target}$ essential for any growth on either of the carbon sources. While metabolizing carbon source A, the selection slope, defined as V target/VB M at the origin, is 0.5. (D) By changing the carbon source the selection slope is increased, now requiring 1 unit of target flux per biomass flux, and thus a tighter coupling. (E) Phenotypic phase space depiction of the feasible fluxes for each metabolic configuration. While the unmodified network allows biomass to be generated independently from the target flux (gray line), by eliminating reactions V1 and V3 the flux space is reduced only to flux modes in which biomass generation is coupled to the target flux; either with weak or strong coupling slope (purple and cyan lines, respectively) (F) If several alternatives lead to coupling, choosing knockouts combination that yields variable selection slopes on different carbon sources (red circle) is preferred, thus giving the experimenter options to increase the selection stringency in steps.

Figure 7A:
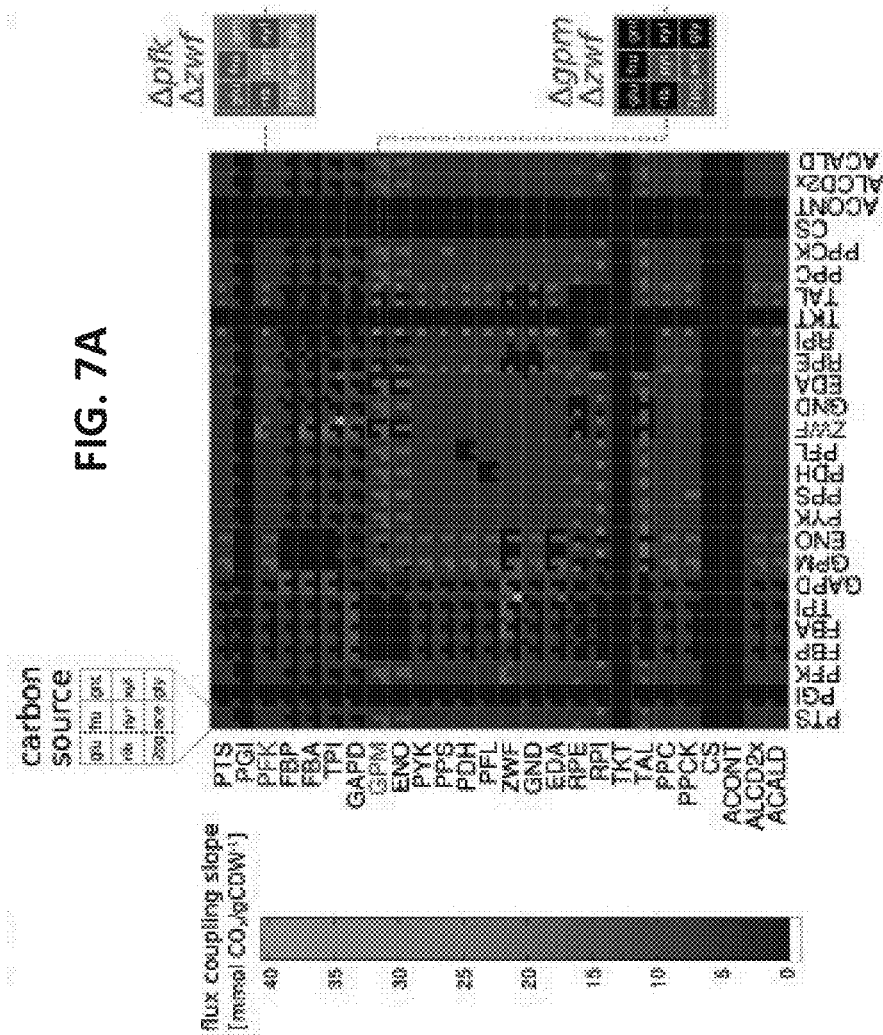
Figure 7B:
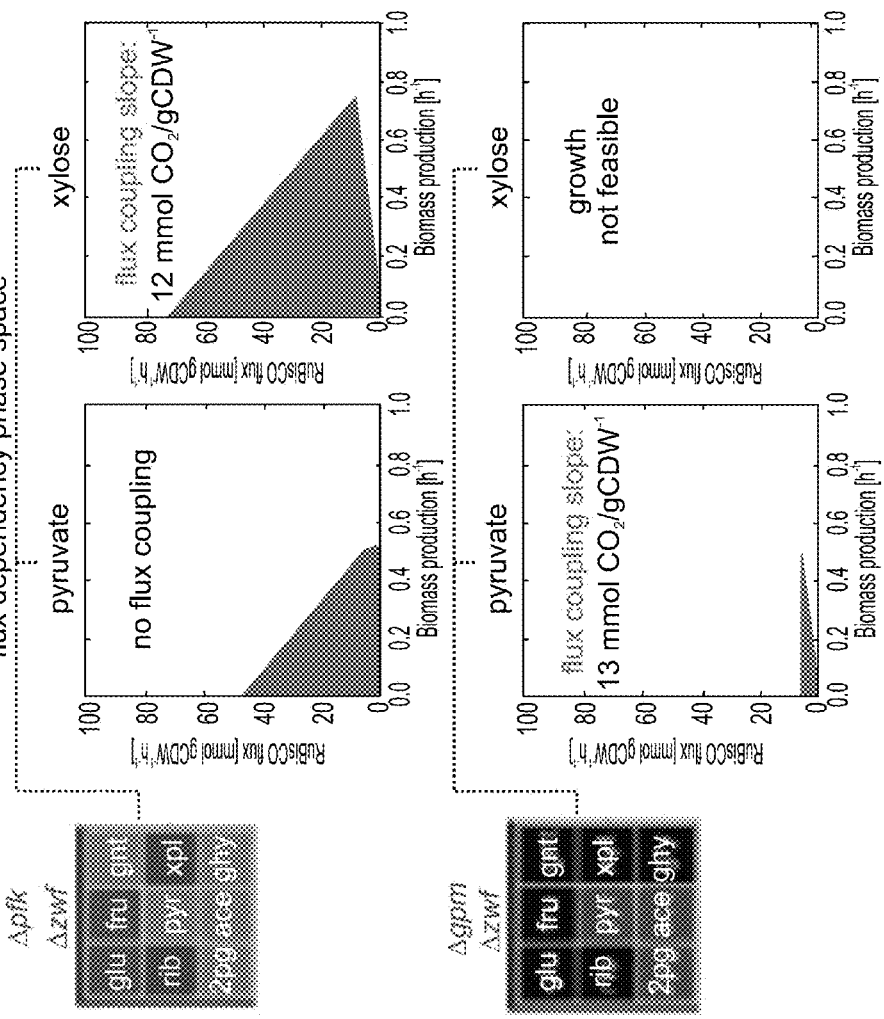

FIGS. 7A-B illustrate a systematic approach for identifying metabolic configurations, in which carbon fixation activity is essential for cell growth. (A) Each block (3×3 yellow grid) refers to a combination of two metabolic reactions to be knocked out within central carbon metabolism of E. Coli. The present inventors analyze the possible growth for each combination of reactions double knockout under 9 different carbon sources. The level of target flux dependence on biomass production is shown using a color code. Feasible fluxes are calculated for the perturbed metabolic network (Methods and FIGS. 6A-F) using each of the nine different carbon sources as exchange inputs (in addition to $CO_2$). Metabolic configurations (a specific combination of knockout mutations and carbon source), in which carbon fixation activity is essential for cell growth are highlighted in green. The selection slope is defined as the minimal carbon fixation flux, required per unit of biomass produced. Higher slope (bright green), refers to a higher carbon fixation activity required for cell growth. Grey cells refer to configurations in which carbon fixation is not essential for growth, while black cells are configurations where growth is not possible. (B) The flux dependency phase spaces of four metabolic configurations (red boxed cells). A mutant which lacks the enzymatic activities of phosphofructokinase (pfkA, pfkB) and glucose6phosphate dehydrogenase (zwf) is predicted to grow on pyruvate (top, left) but without a need to use the target RuBisCO flux. In contrast, it will require the expression of RuBisCO and prk to metabolize pentoses (e.g. xylose, topright). An interesting scenario is the combined knockout of glucose6phosphate dehydrogenase (zwf) and phosphoglycerate mutase (gpmA, gpmM). In this mutant, expression of CBB enzymes allows growth on carbon sources which enter central carbon metabolism through lower glycolysis (e.g. pyruvate, bottom left). The metabolic cutoff prevents gluconeogenic carbon flow which supplies biomass precursors included in upper glycolysis and the pentose phosphate pathway. However, pyruvate can be metabolized in the TCA cycle to generate ATP and reducing power, hence supplying the energy to allow carbon fixation using the CBB cycle thus achieving a growth mode we term semiautotrophic growth. The RuBisCO dependent assimilation of $CO_2$ into biomass, supplies the demand for those biomass precursors which cannot be synthesized from organic carbon in a Δgpm Δzwf mutant in order to allow growth. The present inventors aimed to experimentally test this metabolic scenario. Uptake rate was set to 10 mmol gCDW1h1 for xylose, and 16.7 for pyruvate.

FIG. 8 is a schematic representation of the main sinks for biomass precursor metabolites in central carbon metabolism. 12 precursor metabolites in glycolysis and the TCA cycle serve as metabolic branchpoints, in which flux branches out from central carbon metabolism to build the components of the cell's biomass. We detail the percentage (by mass) contributed to the total biomass derived from each of these key metabolites (as calculated based on F. C. Neidhardt et al., Physiology of the bacterial cell, pp. 142, 1990). This serves as a basis for predicting the expected labeled fraction in the semiautotrophic strain. In mutant E. coli lacking the activities of glucose phosphomutase (gpmA,gpmM) and glucose6phosphate dehydrogenase (zwf) central carbon metabolism is divided into two subnetworks disconnected in terms of carbon flow between them. Due to the cutoff, heterotrophic growth requires a minimum of two carbon sources: one feeding lower EMP pathway and the TCA cycle (energy module, blue), while the other feeding upper EMP pathway and the pentose phosphate pathway (CBB module, green). The relative percentage of the biomass emanating from precursor metabolites in the CBB module sums to approximately 30% of total biomass in the cell (or almost equivalently, carbon biomass), while the metabolites derived from the energy module contribute the remaining 70%. Involved cells showing a semiautotrophic phenotype, $CO_2$ is the sole carbon input into the CBB module, hence about 30% of the cell's carbon is expected to be supplied from RuBisCO dependent assimilation of inorganic carbon.

Figure 9A:
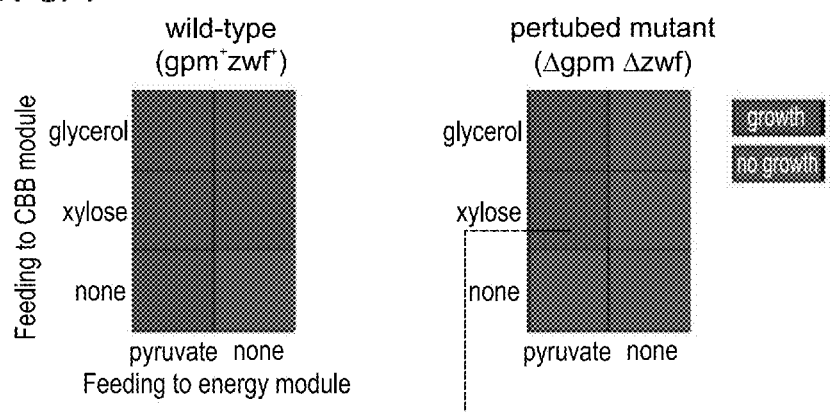
Figure 9B:
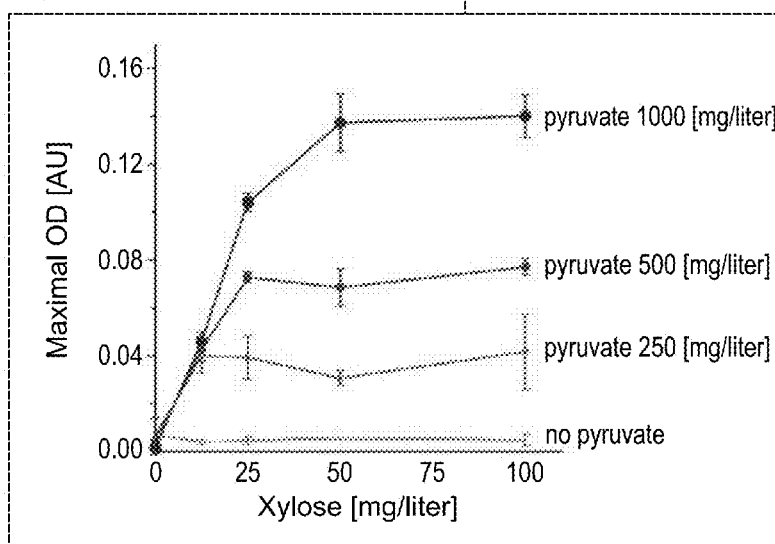

FIGS. 9A-B illustrate carbon source combinations effecting growth and the condition for semiautotrophic growth. (A) Wild type E. Coli cells, with an unperturbed metabolic network, can grow on minimal media supplied with a single carbon source. In contrast, E. Coli mutant lacking glucose phosphomutase (gpmA, gpmM) and glucose6phosphate dehydrogenase (zwf) activities requires a minimum of two carbon sources, each feeding into one of the two disconnected sub networks formed by the metabolic cut off. While two carbon sources are supplied (e.g., xylose and pyruvate), lack of either one would limit growth, even in excess of the other. As shown in FIG. 9B, per given concentration of supplied pyruvate (feeding the energy module), maximal biomass formation is initially proportional linear to the amount of supplied xylose. However, an excess of xylose beyond the point in which the ratio of carbon sources matches the consumption uptake ratio, does not contribute to the formation of additional biomass since growth becomes limited by the availability of pyruvate.

FIGS. 10A-C illustrate a computational prediction and experimental validation that phosphofructokinase (pfkA, pfkB) mutant is RuBisCO-dependent when growing on pentoses. (A) We systematically explored metabolic perturbations which couple RuBisCO-dependent carbon fixation to cellular growth even while an organic carbon source (e.g., xylose) is feeding the CBB module (as occurs during the initial phase of chemostat evolution). The computational analysis (FIGS. 7A-B) predicts that a mutant lacking the activities of glucose6phosphate dehydrogenase (zwf) and phosphofructokinase (pfkA and pfkB) will require the activity of the CBB recombinant enzymes for growth on pentose sugars, but not on trioses. This result stems from the stoichiometry of the pentose phosphate pathway which converts three pentose sugars into two molecules of fructose6P (F6P) and a glyceraldehyde 3phosphate triose. Downstream glycolysis of F6P requires pfk activity to generate fructose1,6P and feed the glycolytic pathway. Therefore, pfk mutant is predicted not to grow on pentose sugars as a single carbon source. Recombinant expression of RuBisCO and prk creates a pfk independent route from pentoses to trioses through the RuBisCO-dependent carboxylation of ribulose bisphosphate to 3phosphoglycerate, hence rescuing growth. In contrast to pentose metabolism, trioses feeding into glycolysis (e.g., pyruvate, glycerol) do not require pfk activity for catabolism nor for the gluconeogenic biosynthesis of hexose phosphates which takes place via fructose 1,6bisphosphatase (fbp). Uptake rate was set to 10 mmol gCDW1h1f or xylose, and 16.7 for pyruvate and glycerol. (B) To experimentally validate the computational predictions, we constructed Δzwf Δpfk mutants and tested the effect of RuBisCO and prk expression while growing either on pentoses or trioses. As predicted, the RuBisco-dependent bypass is essential for growth on pentoses. On permissive carbon sources such as glycerol or pyruvate, growth is independent from RuBisCO expression. (C) The ancestor strain (ΔgpmAM Δzwf ΔpfkAB:rbcLprk) is dependent on RuBisCO activity even while xylose is feeding the CBB module, as occurs during the initial state of chemostat evolution. Due to the glycolytic cutoff imposed by the lack of gpm activity (FIG. 1) the ancestor strain requires a second carbon source feeding into the energy module, in addition to xylose.

Figure 11B:
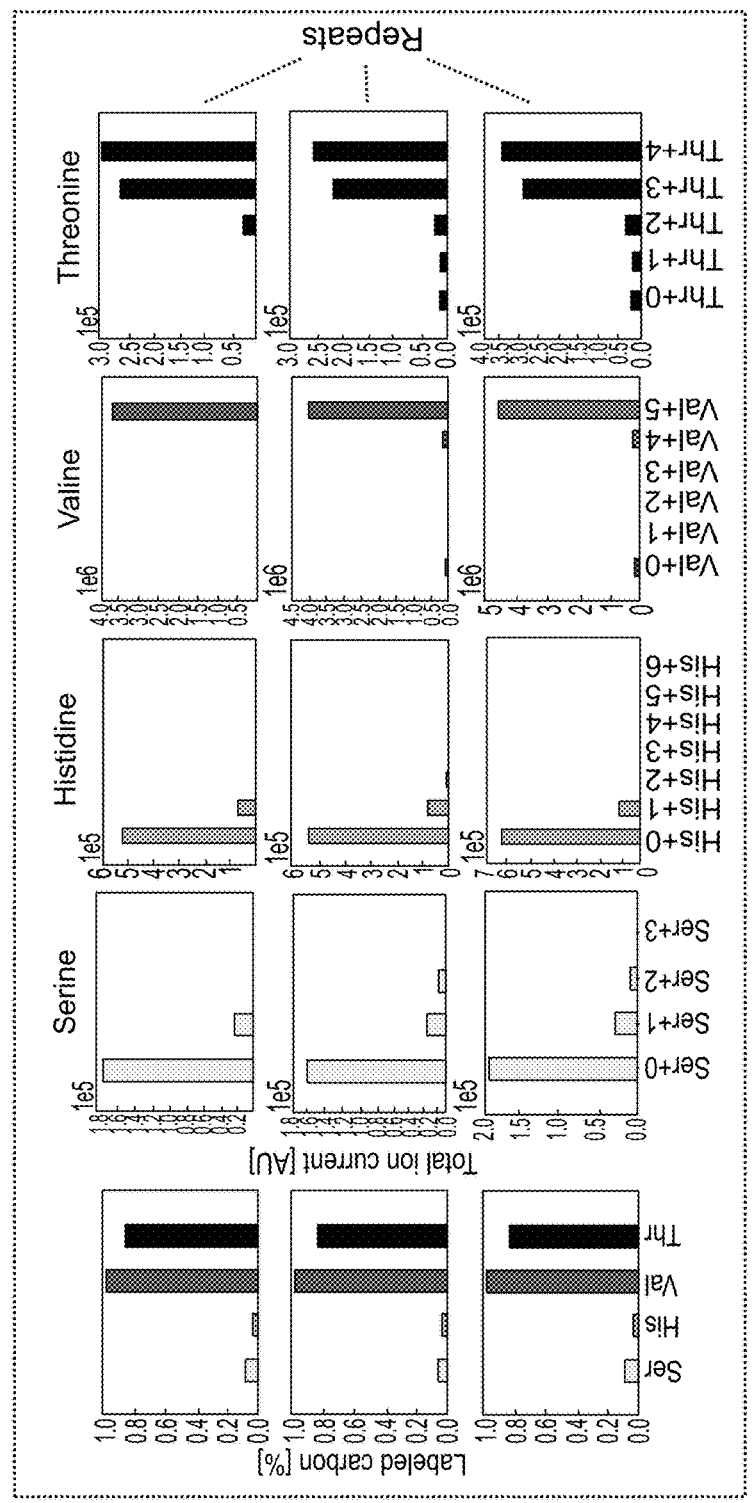
Figure 11C:
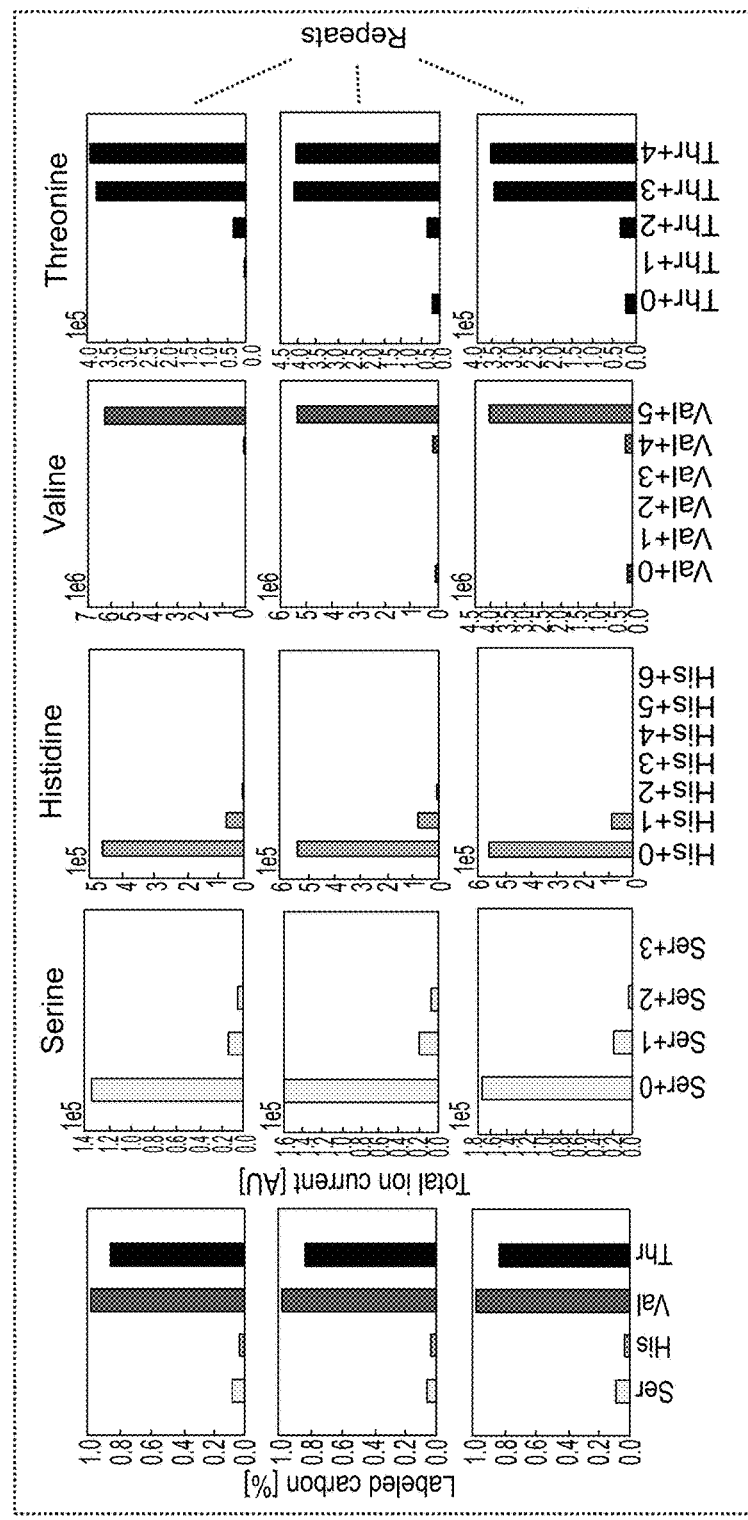
Figure 11D:
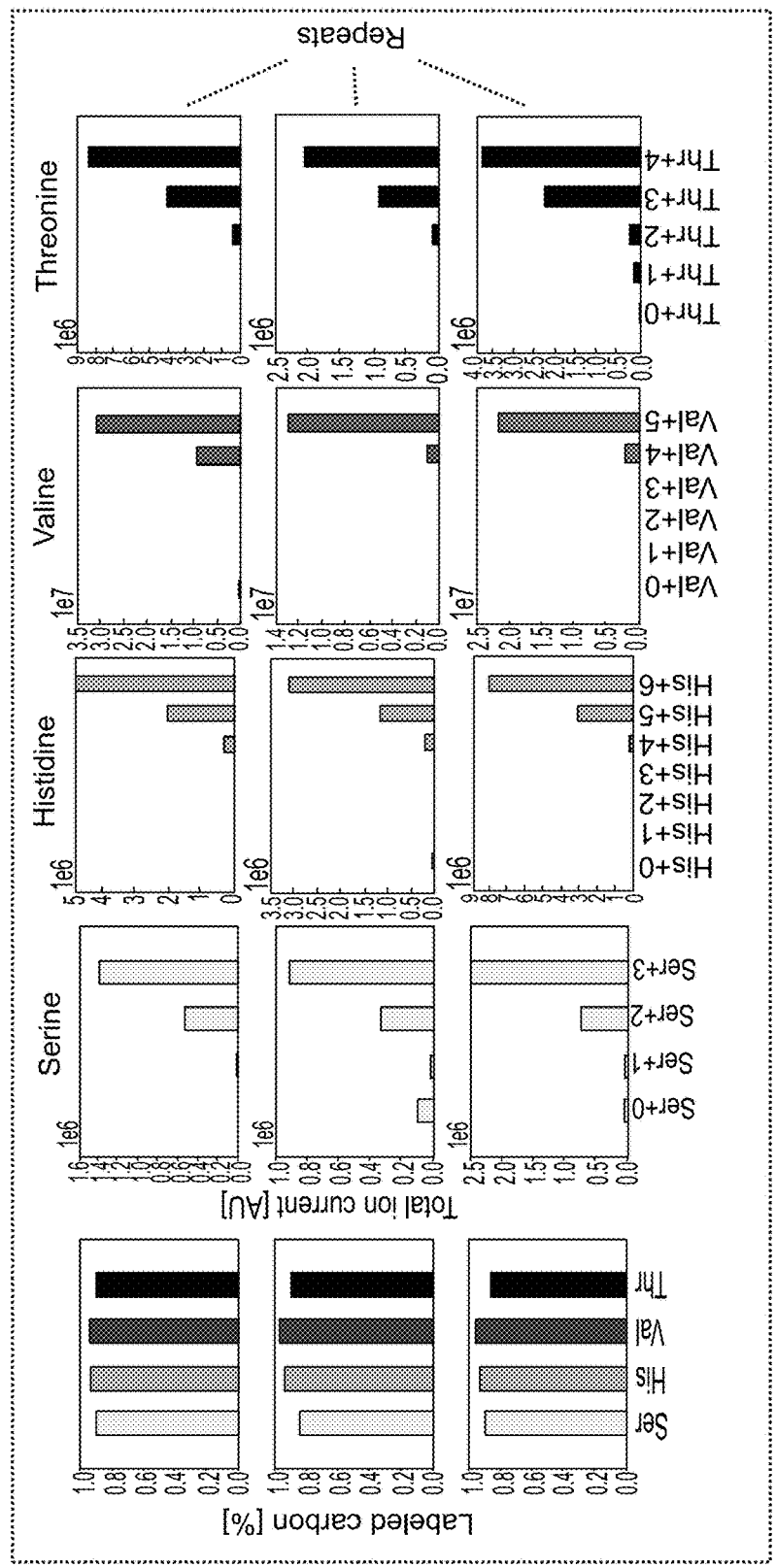

FIGS. 11A-D illustrate mass isotopomer distributions shows fixation of unlabeled $CO_2$ when cells are grown on fully labeled pyruvate. (A-C) Clones displaying semiautotrophic phenotype (i.e., capable of growing on pyruvate and $CO_2$) were isolated from three independent chemostat experiments. Cells were cultured on M9 minimal media containing no organic carbon except uniformly labeled $^{13}C$ pyruvate (5 g/L), in gas controlled environment with 0.1 atm nonlabeled $CO_2$ (Methods). Mass spectrometry analysis of amino acids derived from precursor metabolites originating either from the CBB module (serine, histidine) or the energy module (valine, threonine) shows the expected labeling pattern from semiautotrophic growth mode: trace labeling in serine and histidine synthesized from unlabeled $CO_2$, in contrast to full labeling in valine and threonine which are synthesized from organic carbon. (D) In wild type sample all amino acids are fully labeled since they are directly synthesized from the labeled pyruvate. FIG. 11A: Isolated from first chemostat experiment, day 50; FIG. 11B: Isolated from second chemostat experiment, day 130; FIG. 11C: Isolated from third chemostat experiment, day 70; FIG. 11D: Wild-type control.

Figure 12:
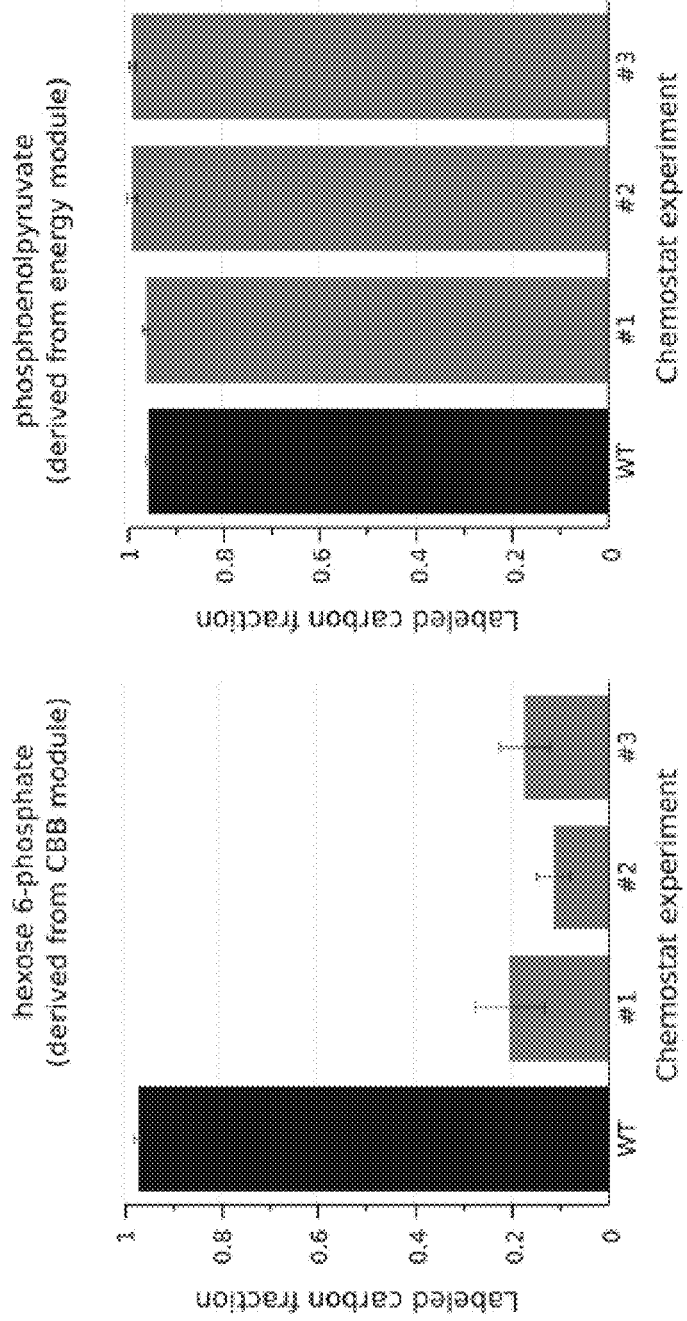

FIG. 12 illustrates a mass spectrometry analysis of intracellular metabolites pool validates CBB cycle dependent biosynthesis of biomass precursors from $CO_2$. Clones isolated from three independent chemostat experiments were cultured in minimal media supplemented only with uniformly labeled $^{13}C$ pyruvate and non labeled $CO_2$. Intracellular metabolites were extracted from samples taken during exponential growth, and analysed using mass spectrometry (Methods). Hexose phosphates (i.e., glucose6phosphate, fructose6phosphate) resulting from the assimilation of $CO_2$ in the CBB module were not labeled, while phosphoenolpyruvate, resulting from pyruvate metabolism in the energy module, was fully labeled. This result is in line with the expected labeling pattern from a semiautotrophic growth mode, in which CBB cycle intermediate are originated solely from the assimilation of inorganic carbon.

Figure 13B:
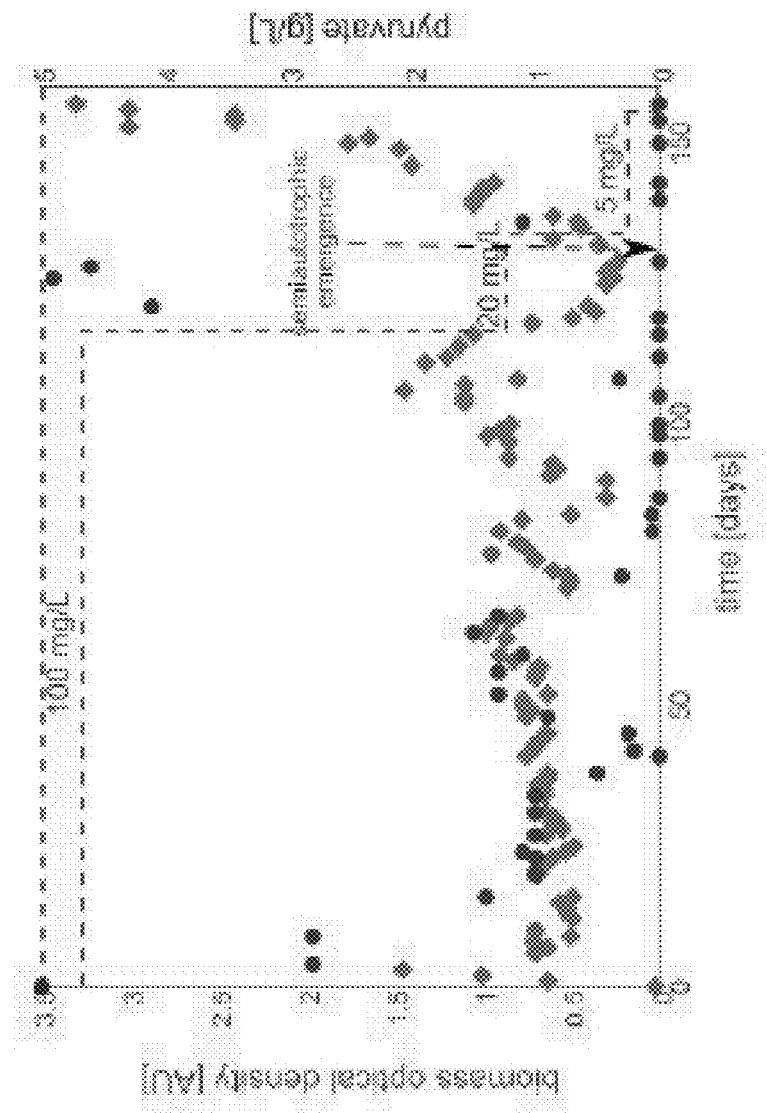
Figure 13C:
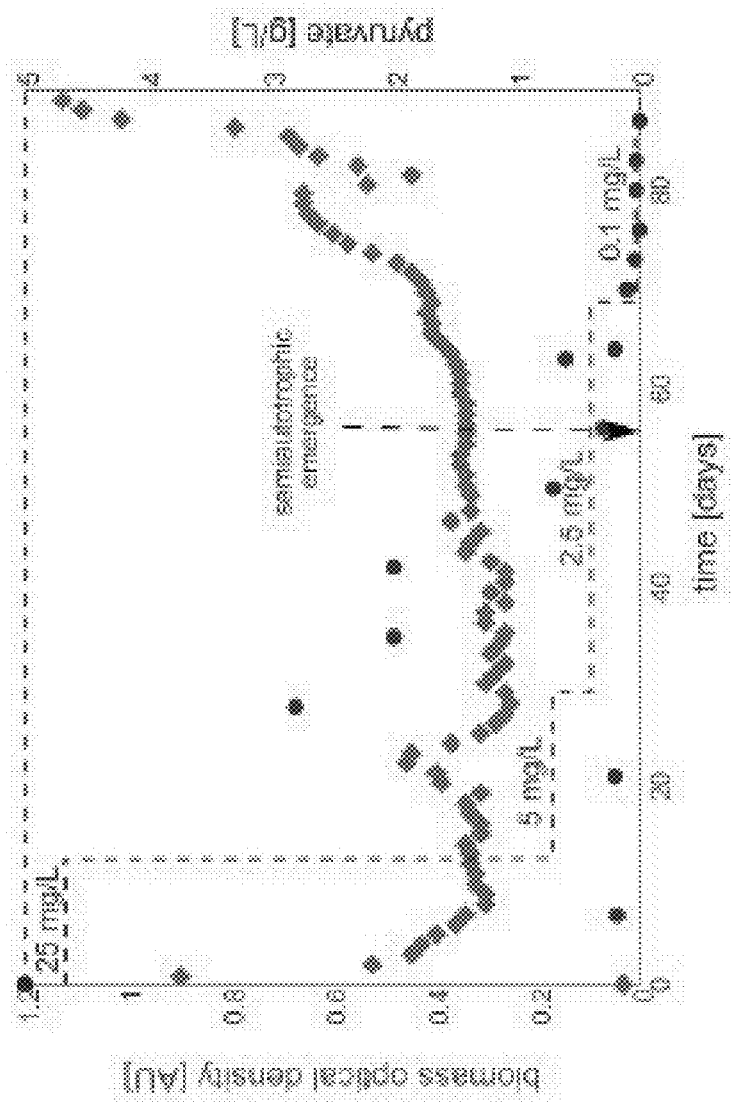

FIGS. 13A-C illustrate evolution dynamics of *E. Coli* towards semiautotrophic growth in three independent chemostat experiments. (A) Ancestor strain (Δpfk Δgpm Δzwf: rbcLprk) was cultured in xylose limited chemostat with a dilution rate of 0.08 h1 (Methods). Xylose concentration in the feed media was kept constant at 100 mg/L (purple dashed line). Pyruvate, the organic substrate feeding the energy module, was provided in excess and its concentration in the feed media was 5 g/L. The residual concentration of these carbon sources, and the cell density inside the chemostat were measured by routine sampling. Once initial steadystate was reached, residual xylose concentration fell below detection limit, while cell density remained relatively constant for the next 50 days. From this point onwards, cell density increased while the residual pyruvate levels decreased. In addition, culture samples from day 50 onwards were able to grow on liquid M9 minimal media, as well as on agar plates, in elevated $CO_2$ conditions (p$CO_2$=0.2) while supplemented solely with pyruvate. The number of colonies formed increased from day 50, reaching saturation at approximately day 70. (B) In the second experiment, the ancestor strain was propagated in the same conditions excluding xylose feed regime. Here xylose concentration was decreased in the feed media whenever residual pyruvate concentration in the culture fell below detection limit, avoiding the possibility that pyruvate becomes the limiting nutrient instead of xylose. Clones with semiautotrophic phenotype were first isolated on day 130. Xylose was completely omitted from the feed media from day 150 onwards, validating the ability of cells to grow in the complete absence of an organic carbon source feeding into the CBB module. Every two weeks culture samples were collected, and later subjected for wholegenome wholepopulation sequencing. (C) For the third experiment, the ancestor strain was further modified by knocking out a component of mismatch repair system (mutS) known to drastically increase the mutation rate. In addition, the dilution rate was set to 0.035 h1. Xylose concentration in the feed was set to 25 mg/L and reduced whenever pyruvate concentration in the culture approached the detection limit as described before. Clones displaying semiautotrophic phenotype were isolated from day 55 onwards.

DESCRIPTION OF SPECIFIC EMBODIMENTS OF THE INVENTION

The present invention, in some embodiments thereof, relates to recombinant non-autotrophic microorganisms that are capable of carbon fixation.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Carbon fixation is the process by which carbon dioxide is incorporated into organic compounds. In the process of transforming sunlight into biological fuel, plants absorb carbon dioxide using over 70% of the fresh water utilized by humanity and the majority of cultivatable land resources on earth. These figures point to the central place that carbon fixation by plants plays in our global ecological footprint.

Carbon fixation in plants and algae is achieved by the Calvin-Benson Cycle (CBBC). The productivity of the Calvin-Benson cycle is limited, under many conditions, by the slow rate and lack of substrate specificity of the carboxylating enzyme Rubisco. As carbon fixation has been shown to limit growth rate in many studies, the present inventors sought to develop alternative pathways that can support carbon fixation in organisms whose genome can be easily manipulated such as $E.$ $Coli$, with the aim to using such bacteria as a platform to experimentally investigate different aspects of the carbon fixation pathways. For example, the microorganism can be used as a screen for identifying engineered enzymes for enhanced carbon fixation properties. Once identified, such enzymes may be expressed in naturally occurring carbon fixating organisms (such as plants) so as to improve carbon fixation.

To accomplish that, the present inventors expressed the two enzymes of the Calvin-Benson cycle which are absent in wild-type $E.$ $Coli$: phosphoribulokinase (PRK) and ribulose-1,5-bisphosphate carboxylase/oxygenase (RuBisCO). Upon expressing the two necessary genes, the present inventors were able to detect PRK- and RuBisCO-dependent assimilation of inorganic $^{13}CO_2$. However, this activity was found to be unstable; after less than 50 generations of continuous cultivation at heterotrophic conditions, cells lost all newly gained carbon fixation activity (FIGS. 5A-B). This could be attributed to the protein load imposed by the overexpression of the foreign genes, whose activities do not contribute bacterial fitness when the endogenous metabolic network remains intact.

The present inventors therefore systematically explored all gene deletions that result in the activities of PRK and RuBisCO being essential even for a heterotrophically grown bacterium using a constraint-based modeling framework (FIGS. 6A-F and 7A-B). From the in silico results, the present inventors established that by combining several gene transfer events, and gene deletions, it is theoretically possible to produce an $E.$ $Coli$ strain which obtains its energy from metabolizing an organic compound, while building a portion of its cellular building blocks from carbon fixation.

The present inventors implemented this strategy and engineered a number of different $E.$ $Coli$ strains which expressed two disconnected sub-networks of central metabolism—(1) the CBBC-module, containing the upper glycolysis, the pentose phosphate pathway and the two foreign enzymes; (2) the energy-module, containing the lower glycolysis and the TCA cycle. However, these strains failed to grow semiautotrophically at elevated $CO_2$, when supplied only with a substrate of the energy-module.

Thus, for example the present inventor showed that the ΔpfAΔpfkBΔgpmAΔgpmMΔzwf:PRK-RuBisCO strain was able to grow only in the presence of two carbon sources; one which enters the CBBC-module and the second which enters the energy-module, e.g., xylose and pyruvate, respectively.

The present inventors hypothesized that the while all the necessary enzymatic components for carbon fixation were present and active, the organism failed to grow semiautotrophically (in the absence of xylose) because a fine tuning of flux distribution is required to support a well-balanced activity of an autocatalytic cycle (a cycle whose product is an intermediate of the cycle), such as the CBBC.

Hence, the present inventors harnessed the natural selection of the $E.$ $Coli$ to optimize and balance pathway activity towards establishing semiautotrophic growth. They cultivated the cells in an environment in which the substrate of the energy-module, as well as $CO_2$, are in excess, while the substrate of the CBBC-module is limiting. This, they showed, imposed a strong selective pressure on the cells to become dependent on the carbon fixation activity of the CBBC: Semiautotrophs which no longer required the organic substrate of the CBBC-module took over the population.

Thus according to a first aspect of the present invention there is provided a microorganism which is genetically modified so that it produces a first essential biomass precursor by metabolizing $CO_2$ using a recombinant carbon fixation enzyme, wherein the microorganism produces a second biomass precursor by metabolizing an organic carbon source and not by metabolizing $CO_2$, wherein the microorganism does not use the organic carbon source for producing the first essential biomass precursor.

The microorganism of this aspect of the present invention generates ATP and a reducing power (e.g. NADH) via metabolism of the organic carbon source.

As used herein, the term "microorganism" refers to any organism of microscopic size which, in its native state, is not capable of biosynthesizing metabolites by utilizing $CO_2$ solely as a carbon source.

Thus, for example the scope of the present invention does not include cyanobacteria or *Rhodospirillum Rubrum*, which are capable of carbon fixation in their native state. Non-limiting examples of microorganisms include both prokaryotic and eukaryotic microorganisms, such as bacteria, archae, protozoan, fungi, molds, yeasts, algae etc. The microorganism may be aerobic or anaerobic.

The organisms can be fermentative organisms. Exemplary microorganisms include, for example, *Clostridium* (e.g., *C. acetobutylicum*, *C. Beijerinckii*, *C. saccharoperbutylacetonicum*, *C. saccharobutylicum*, *C. aurantibutyricum*, *C. tetanomorphum*), *Zymomonas*, *Escherichia* (e.g., *E. Coli*), *Salmonella*, *Rhodococcus*, *Pseudomonas*, *Bacillus*, *Lactobacillus*, *Enterococcus*, *Alcaligenes*, *Klebsiella*, *Paenibacillus*, *Arthrobacter*, *Corynebacterium*, *Brevibacterium*, *Pichia*, *Candida*, *Hansenula*, *Zymomonas* and *Saccharomyces*, e.g., *Saccharomyces cerevisiae*, *Saccharomyces carlsbergensis*, *Kluyveromyces lactis*, *Saccharomyces lactis*.

The bacteria may be those which are useful in the food industry. For example lactic Acid Bacteria (LAB) play an essential role in the preservation, taste and texture of cheese, yogurt, sausage, sauerkraut and a large variety of traditional indigenous fermented foods.

Bacteria may be gram positive or gram negative. Examples of bacteria which are contemplated by the present invention include, but are not limited to *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus*, and *Zymomonas*.

Examples of fungi contemplated by the present invention include, but are not limited to *Aspergillus, Candida, Chlamydomonas, Chrysosporium, Cryotococcus, Fusarium, Kluyveromyces, Neotyphodium, Neurospora, Penicillium* (e.g. *P. chrysogenum*), *Pichia, Saccharomyces, Trichoderma* and *Xanthophyllomyces*.

The term "carbon fixation" as used herein refers to a process through which inorganic carbon (e.g. gaseous carbon dioxide or bicarbonate) is assimilated into an organic backbone. Carbon fixation results in the transfer from an inorganic carbon pool to an organic cellular carbon pool.

The term "enzyme" as used herein refers to a "catalytically functional biomolecule," which includes both whole native (or native-size) molecules, naturally occurring enzymes and derivatives (e.g. genetic modifications) thereof.

As used herein, the phrase "carbon fixation enzyme" refers to an enzyme which is part of a carbon fixation pathway or cycle.

As used herein the phrase "carbon fixation pathway" refers to a set of molecules (e.g. enzymes, electron donors, co-factors etc.) that together enable carbon fixation. The pathway may be linear or cyclical.

An exemplary carbon fixation pathway is the Calvin-Benson-Bassham (CBB) Cycle.

This cycle can be divided into three phases:

Phase 1:

Carbon fixation. The enzyme Rubisco (ribulose bisphosphate carboxylase) catalyses the carboxylation of ribulose-1,5-bisphosphate in a two step reaction. Ribulose-1,5-bisphosphate must first be phosphorylated by the enzyme Phosphoribulose kinase. The outcome of this carboxylation are two molecules of 3-Phosphoglycerate.

Phase 2:

Reduction. 3-Phosphoglycerate is then phosphorylated with the aid of the enzyme phosphoglycerate kinase to yield 1,3-Bisphosphoglycerate. Next 1,3-Bisphosphoglycerate is reduced by NADPH to yield NADP$^+$ and Glyceraldehyde-3-phosphate with the aid of Glyceraldehyde-3-phosphate dehydrogenase. One of every six Glyceraldehyde-3-phosphate molecules is exported into the cytoplasm to be use in the synthesis of Glucose and other metabolic processes.

Phase 3:

Regeneration of ribulose. Glyceraldehyde-3-phosphate is then reversibly converted to Dihydroxyacetone phosphate by Triose phosphate isomerase. Next Dihydroxyacetone is converted into fructose-6-phosphate (F-6-P) by Aldolase and Fructose bisphosphatase. Aldolase condenses the two DHAP molecules to form Fructose-1,6-bisphosphate. Because of its high (−)delta G the transformation of Fructose-1,6-bisphosphate to Fructose-6-phosphate is thought to be the rate limiting step of the CBB cycle. F-6-P can then be converted into glucose via two enzymatic steps with the help of Phosphoglucoisomerase and glucose-6-Phosphatase. Dihydroxyacetone can also go on to condense with Erythrose-4-phosphate to form Sedoheptulose-1,7-bisphosphate (SBP). This reaction is also catalyzed by Aldolase. SBP is then de-phosphorolated by Sedoheptulose bisphosphatase to yield Sedoheptulose-7-phosphate (S7P). After several rearrangement reactions utilizing Transketolase and Transaldolase enzymes, Xylulose-5-Phosphate (X5P) and Ribose-5-phosphate (R5P) are synthesized. Lastly X5P and R5P are isomerised by Phosphopentose epimerase and Phosphopentose isomerase to yield Ribulose-5-phosphate which can then be put back into the cycle.

According to particular embodiments, the microorganism is genetically modified to express at least one enzyme of a carbon fixation pathway (e.g. Calvin-Benson-Bassham (CBB) Cycle) such that the carbon fixation pathway is active in the microorganism (i.e. utilizes carbon dioxide through the non-native carbon fixation pathway) for the production of an essential biomass precursor. As such the recombinant enzymes of this aspect of the present invention are expressed such that they are positioned relative to one another such that they are able to function to cause carbon fixation. According to this embodiment the enzymes which take part in the carbon fixation pathways are present in the same component of the cell such that they are able to cooperate with one another in order to fulfill their role in the carbon fixation pathway.

The exact carbon fixation enzymes to be expressed in a particular microorganism will vary according to the enzymes which are natively expressed in that microorganism.

Thus, for example, out of the 12 reactions of the CBBC, only two are catalyzed by enzymes which are absent in *E. Coli*: phosphoribulokinase (PRK; EC 2.7.1.19) and ribulose-1,5-bisphosphate carboxylase/oxygenase (RuBisCO). The remaining reactions are catalyzed by the native gluconeogenic and pentose phosphate pathway's enzymes. Notably, while *E. Coli* does not contain sedoheptulose-bisphosphate aldolase and sedoheptulose-bisphosphatase, these can be bypassed by the native transketolase enzyme. Thus, for *E. Coli*, the present invention contemplates expressing both PRK and RuBisCO.

The enzymes may be of any origin.

Thus an enzyme of the present invention also refers to homologs and other modifications including additions or deletions of specific amino acids to the sequence (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to the native amino acid sequence of the enzyme, as determined using BlastP software of the National Center of Biotechnology Information (NCBI) using default parameters). The homolog may also refer to an ortholog, a deletion, insertion, or substitution variant, including an amino acid substitution, thereof and biologically active polypeptide fragments thereof.

Thus RuBisCo may for example be a *Rhodospirillum rubrum* RuBisCo being encoded by a sequence as set forth in SEQ ID NO: 1 or having an amino acid sequence as set forth in SEQ ID NO: 4. The amino acid sequence may be at least 90% identical, at least 91% identical, at least 92% identical, at least 93% identical, at least 94% identical, at least 95% identical, at least 96% identical, at least 97% identical, at least 98% identical, at least 99% identical to SEQ ID NO: 4.

The PRK enzyme may be *Synechococcus* PRK being encoded by a sequence as set forth in SEQ ID NO: 2 or having an amino acid sequence as set forth in SEQ ID NO: 5. The amino acid sequence may be at least 90% identical, at least 91% identical, at least 92% identical, at least 93% identical, at least 94% identical, at least 95% identical, at least 96% identical, at least 97% identical, at least 98% identical, at least 99% identical to SEQ ID NO: 5. Alternatively, the RuBisCo and PRK may be expressed using an operon of the proteobacteria *Ralstonia eutropha*, which contains all the Calvin-Benson Cycle genes in tandem.

According to a particular embodiment, the RuBisCo is a plant-derived RuBisCo.

The present inventors further contemplate expressing a recombinant carbonate dehydratase in the microorganisms of the present invention. By doing so, the microorganism becomes capable of utilizing inorganic carbon which is present in the bicarbonate form in order to generate the first biomass precursor.

The carbonate dehydratase may be a *Rhodospirillum rubrum* carbonate dehydratase being encoded by a sequence as set forth in SEQ ID NO: 3 or having an amino acid sequence as set forth in SEQ ID NO: 6. The amino acid sequence may be at least 90% identical, at least 91% identical, at least 92% identical, at least 93% identical, at least 94% identical, at least 95% identical, at least 96% identical, at least 97% identical, at least 98% identical, at least 99% identical to SEQ ID NO: 6.

To express the enzymes of the present invention using recombinant technology, a polynucleotide encoding the enzymes is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

The polynucleotide may further comprise ribosome binding sites to differentially control the expression level of the genes. Thus, for example for rbcL, the ribosome binding site rbs-C may be used, for prkA the ribosome binding site rbs-Emay be used and for CA the ribosome binding site rbs-C may be used.

Thus, the present invention contemplates isolated polynucleotides encoding the enzymes of the present invention.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exon sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Nucleic acid sequences encoding the enzymes and enzyme activating proteins of some embodiments of the invention may be optimized for expression for a particular microorganism. Examples of such sequence modifications include, but are not limited to, an altered G/C content to more closely approach that typically found in the microorganism species of interest, and the removal of codons atypically found in the microorganism species commonly referred to as codon optimization.

The phrase "codon optimization" refers to the selection of appropriate DNA nucleotides for use within a structural gene or fragment thereof that approaches codon usage within the microorganism of interest. Therefore, an optimized gene or nucleic acid sequence refers to a gene in which the nucleotide sequence of a native or naturally occurring gene has been modified in order to utilize statistically-preferred or statistically-favored codons within the microorganism. The nucleotide sequence typically is examined at the DNA level and the coding region optimized for expression in the microorganism species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed genes, followed by a calculation of the average squared deviation. The formula used is: 1 SDCU=n=1 N [(Xn−Yn)/Yn]2/N, where Xn refers to the frequency of usage of codon n in highly expressed genes, where Yn to the frequency of usage of codon n in the gene of interest and N refers to the total number of codons in the gene of interest.

One method of optimizing the nucleic acid sequence in accordance with the preferred codon usage for a particular cell type is based on the direct use, without performing any extra statistical calculations, of codon optimization tables such as those provided on-line at the Codon Usage Database through the NIAS (National Institute of Agrobiological Sciences) DNA bank in Japan (wwwdotkazusadotordotjp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, *E. Coli*), a naturally-occurring nucleotide sequence encoding a protein of interest can be codon optimized for that particular species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular species. Therefore, codon optimization of the native nucleotide sequence may comprise determining which codons, within the native nucleotide sequence, are not statistically-favored with regards to a particular plant, and modifying these codons in accordance with a codon usage table of the particular species to produce a codon optimized derivative. A modified nucleotide sequence may be fully or partially optimized for microorganism codon usage provided that the protein encoded by the modified nucleotide sequence is produced at a level higher than the protein encoded by the corresponding naturally occurring or native gene. Construction of synthetic genes by altering the codon usage is described in for example PCT Patent Application No. 93/07278.

As mentioned hereinabove, polynucleotide sequences of the present invention are inserted into expression vectors (i.e., a nucleic acid construct) to enable expression of the recombinant polypeptide. The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Exemplary bacterial based expression systems are disclosed in Baneyx et al., Current Opinion in Biotechnology, 1999; 10, 411-421 and Macrides et al, Microbiol Rev 1996, 60: 512-538, incorporated herein by reference.

Contemplated promoters for expression in bacteria include the l-arabinose inducible araBAD promoter (PBAD), the lac promoter, the l-rhamnose inducible rhaP BAD promoter, the T7 RNA polymerase promoter, the trc and tac promoter, the lambda phage promoter pL, and the anhydrotetracycline-inducible tetA promoter/operator.

The microorganisms may be transformed stably or transiently with the nucleic acid constructs of the present invention. In stable transformation, the nucleic acid molecule of the present invention is integrated into the microorganism genome and as such it represents a stable and inherited trait. In transient transformation, the nucleic acid molecule is expressed by the cell transformed but it is not integrated into the genome and as such it represents a transient trait.

Knock-in methods for expressing a gene in a microorganism are also contemplated.

It will be appreciated that the microorganisms of this aspect of the present invention are not fully autotrophic since they rely on an organic carbon source to produce energy (i.e. ATP). Examples of organic carbon sources include, but are not limited to acetate, pyruvate, malate, succinate, fumarate, oxaloacetate, xylose and citrate. Selection of a particular carbon source will depend on the particular microorganism and the genetic modifications thereof as further described herein below.

As mentioned, the microorganisms of this aspect of the present invention utilize carbon dioxide, which is assimilated via the non-native enzymes, to generate at least one biomass precursor, while utilizing an organic carbon source to generate other (i.e. non-identical) biomass precursors. The "at least one biomass precursor" may be derived from organic carbon sources as well, so long as it is not the same organic carbon source used to generate the "other biomass precursors". By way of an example, the microorganism is modified such that it utilizes carbon dioxide which is assimilated through non-native Calvin cycle enzymes to generate biomass precursors such as 5-phospho-D-ribose α-1-pyrophosphate (PRPP), glucose-6P, fructose-6P, erythrose-4P, 3phophoglycerate, glycerol-3-phosphate and aromatic amino acids (referred to herein as group 1 biomass precursors). Other biomass precursors (e.g. non-aromatic amino acids, also referred to herein as group 2 biomass precursors), are derived from an organic carbon source (e.g. pyruvate). Additional examples of biomass precursors are provided in FIG. 8, the group 1 biomass precursors being colored in green and the group 2 biomass precursors being colored in blue. The group 1 biomass precursors may also be generated from an organic carbon source, so long as it is not the same organic source used to generate the group 2 biomass precursors (e.g. not pyruvate).

According to a particular embodiment, group 1 biomass precursors are derived from carbon dioxide and xylose and group 2 biomass precursors are derived from pyruvate.

According to a yet another embodiment, group 1 biomass precursors are derived from carbon dioxide and glycerol and group 2 biomass precursors are derived from pyruvate.

According to still another embodiment, the organic carbon source from which group 2 biomass precursors are generated does not comprise a hexose or pentose sugar.

In order to prevent the microorganism from utilizing the organic carbon source which is used for energy production (and group 2 biomass precursors) for the generation of group 1 biomass precursors, the microorganism is typically further genetically modified.

Determining which additional genetic modifications should be made to a particular microorganism can be carried out by and identifying sets of knock outs, gene additions and media composition, which ensure that the flux through the carbon fixation pathway is essential for cell growth. This may be effected computationally—e.g. using a constraint-based modeling framework, as described in the Examples section below.

Thus, for example, for *E. Coli*, the present inventors have determined that according to one embodiment, in order to prevent utilization of the organic carbon source which is used for energy production and the generation of group 2 biomass precursors for the generation of group 1 biomass precursors, down-regulation of expression or activity of phosphofructokinase (pfk) or ribose-5-phosphate isomerase (rpi; EC 5.3.1.6) may be effected. Preferably down-regulation of both pfkA (EC 2.7.1.11) and pfkB (EC 2.7.1.105) is effected.

Additionally, or alternatively down-regulation of expression or activity of phosphoglycerate mutase (gpm; EC 5.4.2.11) may be carried out to prevent utilization of the organic carbon source which is used for energy production and the generation of group 2 biomass precursors for the generation of group 1 biomass precursors. Preferably down-regulation of both gpmA and gpmB is effected.

At least one member of the Entner-Doudoroff (ED) pathway and/or the oxidative pentose P pathway may optionally be knocked out (or down-regulated) to enforce Rubisco dependence via PFK. Thus, for example the genes 6-phosphogluconate dehydratase (edd) and ketohydroxyglutarate aldolase (eda) may be knocked out to prevent utilization of the ED pathway and glucose 6-phosphate-1-dehydrogenase (zwf) may be knocked out to prevent utilization of the of oxidative P pathway).

Furthermore downregulation of the operon AceBAK can be effected so as to prevent utilization of acetate for the generation of group 1 biomass precursors. Thus, knock-out of malate synthase A (aceB), isocitrate lyase (aceA) and/or isocitrate dehydrogenase kinase/phosphatase (aceK) is also contemplated.

Down-regulation of expression or activity of genes in the microorganism may be effected using any method known in the art.

Methods of deleting or downregulating genes from the chromosome of microorganisms are known to those of skill in the art and include homologous recombination, knock out techniques, RNAi etc.

For bacteria, methods such as P1 transduction from already existing knockout strains (KEIO collection) or via lambda-phage assisted recombination (Pkd46 system) may be used to knock-out specific genes.

Other methods which include down-regulating genes in microorganisms using CRISPR arrays are also contemplated. These methods are described for example in WO 2012164565, the contents of which is incorporated herein by reference.

For *E. Coli*, the following strains summarized in Table 1 are contemplated:

TABLE 1

| | | | Knockouts | | | | |
| --- | --- | --- | --- | --- | --- | --- | --- |
| KO7 | KO6 | KO5 | KO4 | KO3 | KO2 | KO1 | strain |
| | | glcB | aceBAK | pfkB | pfkA | zwf | #1 |
| pck | pps | glcB | aceBAK | pfkB | pfkA | zwf | #2 |
| | gpmB | gpmA | aceBAK (optional) | pfkB | pfkA | zwf | #3 |
| | | eno | aceBAK | pfkB | pfkA | zwf | #4 |

It is appreciated that the strains described in Table 1 (which have been genetically modified to express phosphoribulokinase (prk) and Ribulose-Bisphosphate Carboxylase (RuBisCo), and optionally carbonate dehydratase may be further modified. This may be effected by performing random mutagenesis on the strains (e.g. as described in the Examples section herein below) and/or by deleting a component of mismatch repair system genes (muts). Such strains may then be propagated under particular conditions so as to harness the natural selection of the *E. Coli* to optimize and balance pathway activity, as further described herein below.

Alternatively, randomly mutated strains of *E. Coli* may be used as the starting material on which the deletions and modifications described herein above are performed.

As mentioned, in order to propagate the microorganisms of this aspect of the present invention, they are cultured in a medium which comprise both an organic carbon source to feed the TCA cycle (for the production of ATP and a reducing power (e.g. NADH) and a non-organic carbon source (e.g. carbon dioxide) to supply the building blocks for biomass precursors originating from upper glycolysis and Pentose Phosphate intermediates—group 1 biomass precursors.

The organic carbon source is selected depending on the particular strain of the microorganism and the genetic modifications carried out. Thus, for strain 1 in Table 1 herein above, the *E. Coli* may be cultured in a medium comprising acetate. For Strains 2, 3 or 4, the *E. Coli* may be cultured in a medium comprising pyruvate, malate, succinate, fumarate, oxaloacetate or citrate. According to one embodiment, the culture medium comprises a single organic carbon source (e.g. pyruvate).

As mentioned, the microorganisms may rely solely on carbon dioxide to supply the building blocks for biomass precursors originating from upper glycolysis and Pentose Phosphate intermediates (group 1 biomass precursors) or may rely on a second organic carbon source (pentose or hexose sugar) together with the carbon dioxide to produce those biomass precursors. The former state is referred to herein as a "semi-autotrophic state".

Contemplated pentose or hexose sugars include for example glycerol or xylose.

Thus according to another embodiment, the culture medium comprises two organic carbon sources (e.g. pyruvate and glycerol; or pyruvate and xylose).

The present inventors have found that in order to generate microorganisms that rely solely on carbon dioxide to supply the building blocks for biomass precursors originating from upper glycolysis and Pentose Phosphate intermediates it is preferable to initially culture the microorganism in a culture which comprises an organic carbon source and a hexose or pentose sugar, wherein the ratio of organic carbon source: hexose or pentose sugar is at least about 10:1. The gas atmosphere may be manipulated such that the carbon dioxide is provided at saturating levels (e.g. at a minimum of 20%).

Preferably, the microorganisms are grown for at least one day, at least two days, at least three days, at least one week, at least one month, at least three months following genetic modification in order for the generation of new strains which are further adapted for semi-autotrophic growth.

The amount of hexose or pentose sugar may be gradually reduced such that eventually, the microorganism relies solely on the carbon dioxide to supply the building blocks for the generation of biomass precursors originating from upper glycolysis and Pentose Phosphate intermediates (group 1).

Typically, the medium also comprises an electron acceptor such as nitrate, sulfate or oxygen at low levels (1-5%). The medium may also comprise appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

According to one embodiment, the microorganisms are cultured on a solid surface—e.g. agarose plates.

The microorganisms may be immobilized on to a solid surface—e.g. filters and the like.

According to another embodiment, the microorganisms are cultured in a bioreactor—e.g. a chemostat to which fresh medium is continuously added, while culture liquid is continuously removed to keep the culture volume constant. By harnessing the natural selection of the *E. Coli* to optimize and balance pathway activity towards establishing semiautotrophic growth, as described herein, the present inventors have generated populations of *E. Coli* with additional mutations. Thus, the present inventors propose deleting (or down-regulating) any one of the genes or intergenic sequences summarized in Tables 2-6 as well as those described herein above in order to generate additional microorganisms of this aspect of the present invention.

Semiautotrophic microorganisms may be further cultured for a suitable length of time, wherein the amount of the first organic carbon source is slowly reduced so that eventually autotrophic microorganisms are produced (i.e. microorganisms that do not require an organic carbon source to generate energy (e.g. ATP)). Typically a source of energy and reducing power is also required for the sustenance of the microorganism. The energy/reducing power source should not provide direct carbon for the growth of the host (otherwise the carbon fixation cycle becomes redundant) i.e. the energy reducing power source should not enable the microorganism to generate the group 1 precursor without being dependent on inorganic carbon dioxide fixation.

Thus, according to another aspect of the present invention there is provided a genetically modified *E. Coli* which expresses a recombinant phosphoribulokinase (prk) and Ribulose-Bisphosphate Carboxylase (RuBisCo) and has deletions in the genes zwf, pfkA and pfkB, the *E. Coli* being an autotroph.

The two best candidates for providing *E. Coli* with reducing power (and energy) are formate and phosphite. The soluble enzyme NAD$^+$-dependent formate dehydrogenase irreversibly oxidizes formate ($E'^0=-430$ mV) and reduces NAD$^+$-formate cannot be directly assimilated by *E. Coli*. NAD:phosphite oxidoreductase irreversibly oxidizes phosphite to phosphate ($E'^0=-650$ mV) and reduces NAD$^+$.

According to a particular embodiment, formate may be used as the source of energy/reducing power as further described in U.S. Application No. 61/913,940, the contents of which are incorporated herein by reference.

The formate which is used may come from any source—e.g., sodium formate, potassium formate, formic acid or formic acid anhydride etc.

Alternatively, and/or additionally, the formate may be generated using electricity. $CO_2$ can be directly reduced at the cathode (the electrons are derived from water splitting at the anode, for example) to generate formate at relatively high efficiency.

In order to generate the formate for use by the microorganism, the microorganism is placed in a bioreactor in a fluid (e.g., water). The cathode may optionally be placed inside the bioreactor in contact with the microorganism. Alternatively, the cathode may be placed in a separate container to the bioreactor and the formate may be channeled to the chamber comprising the microorganism. The fluid may contain other elements required by the microorganism for growth including for example salts, minerals, metals and other nutrients, such as vitamins.

Examples of such bioreactors and further methods are provided in Li et al. Science, 2012, Vol 335, page 1596; Rabaey et al, Current Opinion in Biotechnology, 2011, 22: 371-377; Lovley et al., Current Opinion in Biotechnology, 2011, 22: 441-448; Lovley D. R., Environmental microbiology reports, 2011, 3(1), 27-35; Nevin et al., Microbiology, May/June 2010 Volume 1 Issue 2; Rabaey et al., Applied and Industrial Microbiology, Nature Reviews, October 2010, Volume 8, page 706-716; each of which are incorporated herein by reference.

The electrodes may be fabricated from such conductive polymers and metallic materials including indium tin oxide (ITO), graphite, platinum and silver.

According to one embodiment, the microorganism is one that produces an industrially important product—e.g., a biofuel or a chemical (e.g. astaxanthin). Alternatively, or additionally, the microorganism expresses enzymes such that it is capable of producing an industrially important product—e.g., a biofuel. It will be appreciated that the precise choice of enzymes are selected according to the particular microorganism being used. Alternatively, or additionally, the microorganism expresses an industrially important product—e.g., a recombinant protein. Additional industrial important products include antibiotics or other pharmaceutical, solvents, pigments, food additives, monomers for the plastic industry and industrially valuable polymers.

Biofuels include for example, an alcohol (e.g., methanol, ethanol, propanol, isobutanol, and n-butanol etc.), a hydrocarbon (e.g., an alkane such as methane, ethane, propane, butane, an alkene such as ethylene, propylene, isoprenes, an alkyne such as acetylene etc.) hydrogen, a biodiesel (long-chain alkyl (methyl, propyl or ethyl) esters), an aldehyde or ketones (e.g. acetone, formaldehyde, 1-propanal, etc.). The biofuel can be a solid, a liquid or a gas.

Industrially useful microorganisms include the production of ethanol by *Saccharomyces* and the production of butanol by *Clostridium*.

Other industrially useful microorganisms include those in the production of plastic monomers and solvents.

The recombinant protein may be any protein—e.g., a human protein used for medicinal purposes. Examples of such proteins include an antibody, insulin, interferon, growth hormone, erythropoietin, growth hormone, follicle stimulating hormone, factor VIII, low density lipoprotein receptor (LDLR) alpha galactosidase A and glucocerebrosidase.

As mentioned, in order to express recombinant proteins in the microorganism, polynucleotide sequences encoding same are inserted into expression vectors as described herein above.

It will be appreciated that other than containing the necessary elements for the transcription and translation of the inserted coding sequence (encoding the industrially useful polypeptide), the expression construct for expression of the industrially useful polypeptide can also include sequences engineered to optimize stability, production, purification, yield or activity of the expressed polypeptide.

Depending on the vector and host system used for production, resultant polypeptides of the present invention may either remain within the recombinant cell, secreted into the fermentation medium, secreted into a space between two cellular membranes, such as the periplasmic space in *E. Coli*; or retained on the outer surface of a cell or viral membrane.

Following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site (e.g. 26, 27).

Recovery of biofuels may be recovered according to methods known in the art. Alcohols such as ethanol, methanol, and/or butanol may be recovered from liquid material by molecular sieves, distillation, and/or other separation techniques. For example, ethanol can be concentrated by fractional distillation to about 90% or about 95% by weight. There are several methods available to further purify ethanol beyond the limits of distillation, and these include drying (e.g., with calcium oxide or rocksalt), the addition of small quantities of benzene or cyclohexane, molecular sieve, membrane, or by pressure reduction.

Product gas, for example, as produced by anaerobic metabolism or photosynthesis, may be processed to separate the methane and/or hydrogen components. Methane, hydrogen, or biogas may be drawn off from the system as pipeline gas.

In accordance with the invention, methane and/or hydrogen may be recovered as a biofuel product. Methane may be recovered and/or purified from biogas by known methods and systems which are commercially available, including membrane systems known for separating gases on the basis of different permeabilities. See, for example, U.S. Pat. No. 6,601,543, which is hereby incorporated by reference. Alternatively, various methods of adsorption may be used for separating methane and hydrogen.

Other ways of collecting biofuel products including centrifugation, temperature fractionalization, chromatographic methods and electrophoretic methods.

In certain embodiments, the biofuel recovery/purification components may be integrated into the microorganism culturing system (e.g. bioreactor), for example, by connecting the respective device or apparatus to the gas or liquid effluents from the bioreactors. The purified biofuels and bioenergy products may be stoked in a separate container(s).

Another use of the microorganisms of the present invention is to use them as a screen so as to identify enzymes and/or pathways capable of altering the efficiency of carbon fixation in a plant. Thus, the present invention contemplates expressing in the microorganism carbon fixation enzymes of alternate sources (e.g. plants, fungi etc.) in order to determine whether they have enhanced activity with respect to carbon fixation. According to a particular enzyme, the assay may be used to compare different homologs or variations of a particular enzyme.

Measuring the efficiency of carbon fixation may be performed by analyzing the amount of inorganic carbon assimilation. This may be measured in-vivo by incubating the cells in the presence of isotopic labeled $^{13}CO_2$. The assimilation of inorganic carbon into biomass may be detected via LC-MS analysis of metabolic extracts.

Once a particular enzyme has been identified (e.g. a naturally occurring enzyme, or a mutant enzyme which was generated by mutagenesis, as described herein or appeared via a natural selection in an evolutionary process, as described herein) which shows enhanced properties with respect to carbon fixation in the microorganisms described herein, the present inventors contemplate expressing those enzymes in autotrophic organisms such as plants or algae. It is envisaged that such organisms genetically modified to express these heterologous enzymes will also show enhanced properties with respect to carbon fixation.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Amtzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

As used herein the term "about" refers to +10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A Laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Strains:

Strains in which the metabolic genes were knocked-out were derived from Keio collection[24], *E. Coli* strain BW25113, referred in the text as "wild-type". The genome sequence of the parent used for constructing the ancestor strain, differed from *E. Coli* strain BW25113 in four loci: ptsI (D464N), fabR (V42G), butB (G162A), fhuA (frameshif). These mutations were acquired during early handling of the strain and were discovered during the course of resequencing the evolved clones. The strain inoculated in the chemostat for the evolutionary experiment, referred in the text as "ancestor", contained further genomic modifications: we deleted phosphoglycerate mutase genes (gpmA, gpmM), phosphofructokinase genes (pfkA, pfkB), 6-phosphate-1-dehydrogenase (zwf). In addition, we further deleted the aceBAK operon encoding for the enzymes of the glyoxylate shunt (thus ensuring that a bypass using the tartronate semialdehyde pathway cannot be used to grow on pyruvate as a sole organic carbon source in Δgpm mutant). Detailed information regarding the genotype of clones showing semiautotrophic phenotype which were isolated from chemostat experiments, referred in the text as "evolved isolated clones", appears in Tables 2-6, herein below.

Genomic Modifications:

Multiple gene knockouts were generally obtained by iterative rounds of P1 transductions[25] according to the following procedure: an isolate of the bacteria containing the desired gene deletion, derived from the Keio collection, was purified by single-colony isolation. Gene deletion was confirmed by PCR and the clone was used as a donor for the preparation of the P1 transducing lysate using standard protocols. Upon transduction, recipient strain was grown in agar plates containing a suitable carbon source and supplemented with Kanamycin (Km) as a positive selection for transduction. The introduction of the novel gene deletion was confirmed by checking the size of PCR fragments amplified by a set of primers located upstream and downstream of the targeted deletion(s). When the sizes of the deletion and non-deletion (wild-type) alleles were similar, deletions were validated by direct sequencing of the PCR fragments. Due to the size of the transduced DNA fragment (up to 100 Kbp), it is unlikely that adjacent genes would be deleted via successive rounds of P1 transduction. In such cases we used a lambda RED-mediated gene replacement using a chloramphenicol (Cm) cassette[2]. PCP20, a temperature sensitive plasmid encoding the FLP recombinase, was used according to standard procedures[26] to eliminate the Km or Cm resistance markers, allowing iterative rounds of deletion. After recombinase expression, all gene deletions and the loss of resistance markers were validated using PCR, and the resulting strain was used as the recipient in the next iteration of gene deletion. Whole genome sequencing was used to validate the genotype at the end of the process.

Growth Conditions:

Unless stated otherwise, cells were grown on M9 minimal media supplemented with mentioned carbon sources and chloramphenicol (34 μg/ml). Antibiotics were omitted when validating the ability of evolved semiautotrophic clones to grow solely on pyruvate and $CO_2$. Agar plates were prepared using ultrapure agarose (Hispanagar, Spain). Liquid cultures used for measuring growth curves, were cultured in 96-well plates and incubated at 37° C. in a gas controlled shaking incubator (Infinite M200—Tecan, USA).

Recombinant Expression of RuBisCO and Prk:

For recombinant expression of the CBB cycle components, we constructed a synthetic operon encoding the His-tagged type-II RuBisCO from *Rhodospirillum rubrum* ATCC 11170 (rbcL), His-tagged phosphoribulokinase (prkA) from *Synechococcus elongatus* PCC 7942 and carbonate dehydratase (CA, Rru_A2056) from *Rhodospirillum rubrum* (CA). To differentially control the expression level of rbcL, prkA and CA we placed synthetic ribosome binding sites with varying translation efficiency (rbs-C, rbs-E and rbs-C, respectively) upstream to the open reading frame, as previously described[27]. The synthetic operon was cloned into a pZ vector (Expressys, Germany) with the backbone containing a PLtetO-1 promoter and a p15A medium copy origin of replication. Construct assembly was based on "no-background" cloning methodology previously described[27], with Cm as selective marker. In control experiments, recombinant CBB genes were replaced with an mCherry reporter.

Computational Analysis of RuBiSCO Dependent Strains:

To identify candidate mutants in which cell growth is coupled to the flux through non-native CBB enzymes, we implemented an algorithm based on the principles of flux balance analysis (FBA)[28]. We started by considering all possible combinations of enzymatic reaction knockouts in central metabolism, and filtered out all those combinations that allow growth without any flux in RuBisCO. For those that cannot produce any biomass without RuBisCO, we calculated a slope which is defined as the biomass production rate achieved by allowing a unit of flux in RuBisCO. All other constraints were the same as in standard FBA, where the rate of biomass production is maximized. In more technical terms, the slope is the shadow price[29] of the upper bound on the RuBisCO flux, when that upper bound is set to 0. We implemented our algorithm using the COBRA for Python toolbox[30] and using the *E. Coli* core model (gcrgdotucsddotedu/Downloads/EcoliCore), augmented with the two reactions corresponding to RuBisCO and phosphoribulokinase. It is possible to create a bi-level optimization MILP problem to find the knockout with the highest slope, using the same mathematical principles used in OptKnock[31,32] and RobustKnock[33,34]. However, since we only used the core *E. Coli* model, and had to consider about 20 single knockouts, we chose to explicitly calculate the slope of all possible combinations of one to three knockouts. The total runtime was less than 3 hours on a single Intel™ Core-i7 CPU.

Random Mutagenesis:

A single colony of the ancestor strain was inoculated into 10 mL of M9 media with 5 g/L pyruvate, 0.2 g/L xylose, 2.5 g/L sodium bicarbonate and 34 mg/L chloramphenicol. The culture was incubated overnight in a shaking incubator at 37° C. Subsequently, the cells were harvested and subjected to random mutagenesis using the Aquamutant Mutagenesis Kit (MultiTarget Pharmaceuticals, USA) according to manufacturer instructions. Cells from several mutagenesis intensities regimes (from none to very strong mutagenesis) were pooled and inoculated into the chemostat.

Chemostat Evolution:

We performed a chemostat based laboratory evolution in several independent experiments. In the first and second experiments, bacterial cells following mutagenesis were inoculated into a Bioflo 110 chemostat (New Brunswick Scientific, USA) at working volume of 0.7 L and a dilution rate of 0.08 $h^{-1}$ (equivalent to a doubling rate of 8.75 hours). Feed input was M9 minimal media supplemented with 5 g/L sodium pyruvate, 0.1 g/L xylose and 30 mg/L chloramphenicol at 37° C. The culture was sparged at 0.5 L $min^{-1}$ with a gas mixture containing 25% $CO_2$, 5% $O_2$ and 70% $N_2$. Agitation speed was set to 500 rpm. Biomass density was measured daily and samples for glycerol stocks and the quantification of residual substrate concentrations were collected once a week. To rule out contaminations, culture samples were plated on positive (supplemented with pyruvate and xylose) and negative (glucose) control agar plates. Genetic markers of the ancestor strain were routinely validated in the colonies formed on pyruvate and xylose. No colonies were formed on glucose containing media during the period of the experiment. During the first experiment, the chemostat had a technical malfunction on day 20 and the experiment was restarted using a glycerol stock sample taken on day 18. To avoid the possibility that pyruvate becomes the limiting nutrient instead of xylose, in the second and third experiments, xylose concentrations were lowered in the feed media whenever a drop in residual pyruvate was detected in the culture. The third experiment was performed using a DASBox Bacterial Fermentation system (DASGIP—Eppendorf, Germany). The bacteria were grown in a working volume of 100 ml at a dilution rate of 0.035 $h^{-1}$ (equivalent to 20 hours doubling time). Feed input was the same as described above except that the initial xylose concentration was 25 mg/L. The gassing (0.1 L $min^{-1}$) mixture throughout the entire experiment contained 20% $CO_2$, 10% $O_2$ and 70% $N_2$. The OD, DO, pH and temperature were monitored on-line. Several attempts to perform the evolutionary process resulted in culture contamination after one to 10 weeks and are not reported.

Pyruvate and Xylose Measurements:

Reported results of the residual concentrations of pyruvate and xylose in the chemostat culture were quantified enzymatically with K-PYRUV and K-XYLOSE assay kits (Megazyme, Ireland) respectively. In addition, pyruvate concentrations were validated using an Agilent 1200 series high-performance liquid chromatography system equipped with an anion exchange Bio-Rad HPX-87H column (Bio-Rad, USA). The column was eluted with 5 mM sulfuric acid at a flow rate of 0.6 mL/min at 45° C.

Isotopic Analysis of Hydrolyzed Amino Acids:

Mass isotopologues distributions (MID) can supply information regarding the topology and the fluxes in a metabolic network. By measuring the MID of specific amino acids, it is possible to infer the labeling pattern in precursors metabolites upstream to it in the biosynthesis pathway. For intermediates directly converted to amino acids, hydrolyzed protein samples hold several advantages such as increased throughput and sample stability. For MID analysis, cells were cultured in M9 minimal media, either in the presence of a fully labeled organic carbon source and non-labeled $CO_2$, or in a reciprocal set-up with isotopically labeled $^{13}CO_2$ (Cambridge Isotope Laboratories, USA) and a non-labeled organic carbon source. For experiments in which gaseous $^{13}CO_2$ was used, culture tubes were placed in a transparent air-tight container and flushed with 5 volumes of isotopically labeled gas mixture (10% $^{13}CO_2$ 10% $O_2$ and 80% $N_2$). Cells were incubated in a shaking incubator at 37° C. and harvested during exponential growth. Protein biomass was hydrolyzed with 6N hydrochloric acid using standard protocols. Hydrolyzed amino acids were separated using ultra performance liquid chromatography (Acquity—Waters, USA) on a C-8 column (Zorbax Eclipse XBD—Agilent, USA) at a flow rate of 0.6 mL/min and eluted off the column using a hydrophobicity gradient. Buffers used were: A) $H_2O$+0.1% formic acid and B) acetonitrile+0.1% formic acid with the following gradient: 100% of A (0-3 min), 100% A to 100% B (3-9 min), 100% B (9-13 min), 100% B to 100% A (13-14 min), 1000/% A (14-20 min). Overall run time was 20 minutes. The UPLC was coupled online to a triple quadrupole mass spectrometer (TQS—Waters, USA). Data was acquired using MassLynx v4.1 (Waters, USA). Optimization of ionization parameters and determination of retention times was performed by direct infusion of amino acid commercial standards (Sigma-Aldrich, USA). Argon was used as the collision gas with a flow rate of 0.22 mL/min. Cone voltage was 25V, the capillary was set to 3 kV, source temperature was 150° C., desolvation temperature was 500° C., desolvation gas flow was 700 L/min, source offset 50, cone gas flow was 250 L/min and collision energy was 14 eV. MIDs were detected using multiple reaction monitoring (MRM) with the known molecular masses and the neutral loss of carbonyl carbon as a daughter ion (either 47 or 46 m/z, labeled and unlabeled respectively). Data analysis was performed using TargetLynx (Waters, USA). Total carbon labeling was calculated according to the formula:

$$\text{labeling fraction} = \frac{\sum_{i=0}^{n} m_i * i}{\sum_{i=0}^{n} m_i * n}$$

where $m_i$ is total ion current as measured for the $m_0 \ldots m_n$ masses of each compound.

Isotopic Carbon Ratio in Whole Biomass Samples:

Samples were grown in 500 mL glass flasks in M9 minimal media supplemented with 5 g/L sodium pyruvate. Ancestor strain samples were supplemented with 0.2 g/L xylose in addition to pyruvate. Following inoculation flasks were sealed with rubber septa and flushed with 5 volumes of a gas mixture containing isotopically labeled $^{13}CO_2$. Cells were harvested during exponential growth, washed in M9 minimal media and lyophilized. Between 0.2 and 0.4 mg of each dry biomass sample were weighed into tin capsules and their $^{13}C/^{12}C$ ratio was determined using an elemental analyzer linked to a Micromass (Manchester, UK) Optima IRMS.

Whole-Genome Sequencing:

DNA was extracted from sampled cultures using DNeasy Blood & Tissue kit (QIAGEN, Germany). Samples were prepared for sequencing as previously described[35], with the following modifications: 0.6 μg of DNA was sheared using the Covaris E220x system (Covaris Inc., USA) to fragments of ≈200 bp, followed by ends repair, ligation to adapters, 8-cycles of PCR amplification with Kapa HiFi polymerase (Kapa Biosystems, USA). Samples were sequenced using an Illumina HiSeq 2500 (Illumina, USA) yielding 100 bp paired-end reads. Minimum of 2.5 million reads was obtained per sample, with a mean of 3.5 million reads per sample.

Analysis of Sequence Data.

A reference genome which is based on *E. Coli* strain BW25113[36] (CP009273) and recombinant CBB enzymes encoding the plasmid as a second contig, were prepared. Reads for each sample were mapped independently using BWA[37] (version 0.7.5) with the standard parameters of the reference genome. A 95% unique mapping rate was observed. The mapped reads yielded a mean coverage depth of ×150 per sample and above 99% of the genome was covered with more than ×50. A GATK pipeline[38] was used to perform joint variant calling with all samples. The pipeline included the following steps: (a) Indel realignment using all samples jointly. (b) Variant calling using the Unified Genotyper, assuming a ploidy of 10 for each sample. (c) Standard filtering of SNPs and INDELs to mark suspected artefacts according to GATK Best Practices recommendations. This pipeline infers SNPs and INDELs, assuming a population of cells at a resolution of 10% in the allele frequency. To detect events that are related to the evolutionary process, we compared the frequencies of the alternative alleles between the ancestor and each of the evolved strains. To achieve that, we performed a Fisher exact test on the reference and alternative allele counts between each pair. Allele frequencies at each time point (as shown in FIG. 3A) were estimated using allele counts for the alternative and reference alleles. Fisher test P-values were calculated for all SNP and INDELs. We note, that such analysis does not capture certain types of mutations, such as copy number variation, inversions, or large insertions or deletions. For the detection of large deletions (>100 bp) as well as large sequences (>1000 bp) with high copy number variation, the coverage for each base in each sample was calculated and regions differing by more than three standard deviations of the average coverage in sample were annotated as high copy variation. Regions with a depth below 10 reads were marked as suspected deletions. Loci with poorly determined alternative alleles of isolated clones were revalidated by PCR amplification and Sanger sequencing. All mutations were validated manually using Geneious[39] version 8.0.5 (Biomatters, New Zealand).

Muller Diagrams:

Muller diagrams were automatically generated by a custom program in python. The algorithm receives two inputs: a hierarchical lineage tree (manually inferred from the mutations frequencies and temporal distribution appearing in FIG. 3A to achieve maximal parsimony), and the fraction of every mutation out of the population at each time point. A strain is therefore characterized by the set of mutations that it possesses, but that its ancestor strain does not. Given these two inputs the algorithm first, for every mutation at every time point, rounds it down to 0 if its fraction is smaller than a predefined threshold of 0.005 and given that at neither of the adjacent measurement points the fraction of that mutation is not higher. Next, the algorithm checks, for every mutation, that at every measurement point its fraction out of the population is at least as high as the sum of the fractions of the mutations of its direct descendant strains, where the test is performed recursively. In case this condition fails, the algorithm rounds up the fraction of the mutation to satisfy the constraint. Finally, the algorithm sets, and possibly adds time points to indicate the times at which every mutation arises. If mutation A first appeared in a measurement taken at time $t_i$, then A's initiation time is set to $t_{i-1}$. For every descendant strain of A, if it also first appeared at time $t_{i-1}$, then its initiation time is set to $$\frac{t_i + t_{i+1}}{2}.$$

This procedure then continues recursively for the descendants of each strain whose initiation time was set. At this point the input is being used to generate the muller diagram in the following manner: at every time point, the [0,1] interval is divided to intervals representing the fractions the different mutations occupy out of the population, such that if mutation M has a frequency $f_M$ at the given time point, it will be assigned an interval [a, b] such that b−a=$f_M$. The division is done recursively, starting with the wild type (the ancestor of all the strains) being assigned the entire [0,1] interval. Then, given that mutation M occupies the interval [a, b], and that there are n direct descendant strains to the strain containing M, the unique mutations of these descendent strains are given evenly spaced intervals in [a, b], representing their frequencies, with the space between the intervals of two adjacent descendants being the frequency of M, $f_M$, minus the sum of the frequencies of all of its direct descendants, divided by n+1 (to account of the spaces needed between the first and last descendants) and the boundaries of the interval assigned to M, namely, a and b. For example, if N and L are the only descendants of M and at time point t their fractions are 0.2, 0.4 and 0.75 respectively, and M is assigned the interval [0.2,0.95] then N and L will be assigned the intervals [0.25,0.45] and [0.5,0.9] respectively, so that their intervals are spaced by 0.05 from the boundaries of M's interval and between each other. The recursion then proceeds to the descendants of M until the entire strain hierarchy is covered. Once the intervals are determined for all time points, the algorithm generates the diagram by traversing the strains hierarchy tree. For every strain, identified by its unique mutation, the algorithm draws two lines, one connecting the lower bounds of the intervals of its mutation in time, and the other connecting the upper bounds. The area between these two lines is filled with the color assigned to that mutation. The algorithm then recursively continues to the direct descendants to overlay their area etc. FIG. 3B has been graphically rendered based on the algorithm output in order to clarify locations where mutations occurred and to clearly position adjacent sectors.

Results

The Calvin-Benson-Bassham (CBB) cycle[1] is the gateway to the organic world, being the main pathway for turning inorganic carbon ($CO_2$) into biomass and for storing energy in the biosphere. Heterotrophic organisms are dependent on such supply of organic carbon fixed by autotrophs. How difficult is it to evolve from one trophic mode of growth to another? Specifically, can an obligatory heterotrophic organism be evolved to synthesize biomass directly from $CO_2$? A positive answer will affect our understanding of metabolic plasticity and stimulate exciting avenues towards agricultural productivity[2,3] as well as sustainable production of chemicals[4]. Here the present inventors demonstrate how a combination of rational metabolic rewiring and laboratory evolution under selective environmental conditions leads to the emergence of a fully functional CBB cycle in *E. Coli*. They rewired the metabolic network of an *E. Coli* host by introducing two enzymes (RuBisCO and prk) and severing the glycolysis pathway to decouple carbon-fixation from energy production. After several months under selective conditions in a chemostat, the modified bacteria evolved to semiautotrophic growth, in which carbon fixation via the non-native CBB cycle solely provides all carbons for major biomass building blocks (e.g., serine, histidine, pentose phosphates). Reducing power, energy and the rest of the biomass precursors are obtained by metabolizing a supplied organic compound (e.g., pyruvate). Using whole-genome whole-population sequencing, the evolutionary dynamics until the emergence of the semiautotrophic phenotype are described. The success in evolving a non-native carbon fixation pathway in an obligatory heterotrophic host provides a striking demonstration of the capacity for rapid trophic-mode evolution in metabolism with relevance to biotechnology[5].

The activity of the CBB cycle accounts for >99% of $CO_2$ fixation in the biosphere[6] and dominates agricultural productivity. Out of the 12 reactions of the CBB cycle, only two enzymatic activities are missing in *E. Coli* in order to complete a full cycle: phosphoribulokinase (prk) and ribulose-1,5-bisphosphate carboxylase/oxygenase (RuBisCO). *E. Coli*'s native gluconeogenesis and pentose phosphate pathway enzymes can catalyze all other reactions (FIGS. 1 and 4A-B). Therefore, gene transfer of RuBisCO and prk can equip this heterotrophic host with all the enzymatic machinery required for CBB functionality. Previous efforts have shown functional expression of these enzymes[7-10]. However, full CBB operation in which only $CO_2$ and reducing energy are used as the cycle inputs has so far remained an elusive major challenge[11].

To explore whether the acquisition of only two non-native enzymes is sufficient to establish carbon fixation activity, the present inventors introduced a synthetic operon containing both RuBisCO and prk into an *E. Coli* host (rbcL from *Rhodospirillum rubrum* and prkA from *Synechococcus* PCC6301). Upon expression they were able to detect prk- and RuBisCO-dependent assimilation of inorganic $^{13}CO_2$ into biomass during heterotrophic growth on various carbon sources (Methods). However, this activity was found to be unstable and after less than 50 generations of continuous cultivation the cells lost all newly gained carbon fixation activity (for example, due to toxic effects of CBB cycle intermediates[12,13] or protein burden, FIGS. 5A-B).

Next, they examined whether additional metabolic modifications could ensure a stable fitness advantage of CBB cycle components that will sustain their activity. To identify gene deletions that make RuBisCO-dependent carbon fixation essential for *E. Coli* growth, they computationally analyzed the metabolic effect of RuBisCO and prk expression on various combinations of gene deletions (Methods and FIGS. 6A-F and 7A-B). Their analysis pointed to a novel scenario in which full CBB cycle activity leads to the synthesis of essential biomass precursors using $CO_2$ as the sole carbon source, while energy supply relies on the metabolism of organic carbon (FIG. 1). This scenario goes beyond previously described RuBisCO-dependent strains[8,10] by operating a fully functional CBB cycle in which $CO_2$, ATP and reducing power are the only inputs, as in autotrophic organisms. This mode of growth, not known to occur in nature, was termed semiautotrophic growth.

Out of several design alternatives for semiautotrophic growth, the present inventors decided to experimentally test one possible scenario by severing glycolysis through the deletion of phosphoglycerate mutase (gpmA, gpmM). This deletion effectively separates central metabolism into two disconnected sub-networks (FIG. 1): (i) carbon fixing CBB module, containing upper glycolysis, the pentose phosphate pathway and the recombinant CBB enzymes; (ii) energy module, containing lower glycolysis and the TCA cycle, which supplies ATP and reducing power to drive carbon fixation taking place in the first module. Notably, out of the 12 biomass precursor metabolites from which biosynthetic pathways diverge to supply cellular building blocks[14,15], six are synthesized by the CBB module, and six by the energy module (FIG. 8).

An organic carbon source feeding the energy module, such as pyruvate, could in principle provide reducing power and ATP for carbon fixation, hence allowing the synthesis of biomass precursors in the CBB module from $CO_2$. However, the gpm double mutant expressing RuBisCO and prk failed to grow semiautotrophically at elevated $CO_2$ when provided with a single organic carbon source (FIGS. 9A-B and 10A-C). This strain grew only when a second carbon source feeding the CBB module directly was supplied in addition to pyruvate (e.g., xylose), allowing all biomass precursors to be produced from organic carbon (FIG. 2A left and FIGS. 10A-C). It was hypothesized that given that all the necessary enzymatic components for carbon fixation are present, the failure to grow semiautotrophically can be solved by subjecting the cells to selective conditions favouring full CBB pathway operation. Natural selection can explore multi-knob fine tuning essential for a shift in growth mode, such as changes in regulation, that cannot be currently predicted by rational design.

The present inventors chose to harness natural selection to find the necessary metabolic adjustments by using a chemostat-based evolution experiment that continuously maintained selective conditions for the semiautotrophic phenotype[16]. The ancestor strain for this evolutionary experiment was the double knockout gpm strain expressing RuBisCO and prk, coupled with additional deletions of phosphofructokinase (pfkA, pfkB) and 6-phosphate-1-dehydrogenase (zwf) that make RuBisCO essential for xylose catabolism during heterotrophic growth (FIGS. 2A, 7A-B, 9A-B and 10A-C). The ancestor strain was subjected to random mutagenesis (Methods) and propagated in a xylose-limited chemostat at a dilution rate of 0.08 $h^{-1}$ (doubling time ≈9 hours). The CBB-module substrate concentration in the feed media was set to be strongly limiting ([xylose]=0.1 g/L) while the energy-module substrate and $CO_2$ were supplied in excess ([pyruvate]=5 g/L; $pCO_2$=0.25 atm). The balance of cell growth and dilution rate ensures that the concentration of xylose in the chemostat is extremely low and decreases even further as cells adapt. The scarcity of xylose imposes a strong and continuous selective pressure on cells to overcome the growth limitation by utilizing the abundant form of inorganic carbon (i.e., $CO_2$). It was hypothesized that this selection process will favour the fixation of inorganic carbon in the CBB module and enable a semiautotrophic strain to take over the population[17]. As expected, following inoculation the chemostat became xylose limited: internal xylose concentration in the chemostat was not detectable (<1 mg/L), while the concentration of pyruvate remained in considerable excess (≈2 g/L). Due to Δgpm severing the gluconeogenic pathway, carbon from pyruvate could not enter the carbon fixation module to compensate for the xylose limitation. However, excess pyruvate could serve as a source of energy and reducing power to be utilized by the CBB module, as it evolves to function as a xylose-independent $CO_2$ fixation cycle.

During the first 40 days of growth (≈100 chemostat generations), no significant change in cell density and nutrient concentrations was observed in the effluent media (FIG. 2B). However, over the following 20 days a gradual increase in cell density was noted, accompanied by a steady decrease in pyruvate concentration. Finally, around day 60 (≈150 chemostat generations, FIG. 2B) the concentration of pyruvate dropped to an undetectable level (<1 mg/L). Importantly, in contrast to the ancestor strain, culture samples from day 50 onward (FIG. 2B arrow) formed colonies on minimal agar plates and grew in M9 liquid media (doubling time of ≈6 hours) supplied with only pyruvate and elevated $CO_2$ (FIG. 2C). In ambient $CO_2$, no growth was detected on either liquid media or agar plates. The evolution of clones able to grow solely on $CO_2$ and pyruvate in two other independent chemostat experiments were observed (appearing on day 60 and 130, FIGS. 11A-D).

Isotopic labeling experiments were conducted to test if the source of carbon for the synthesis of CBB-module biomass precursors (in the absence of xylose) results from carbon fixation or by utilizing pyruvate through an evolved Δgpm bypass[18]. The evolved bacteria were cultivated on non-labeled pyruvate and isotopically labeled $^{13}CO_2$ ($p^{13}CO_2$=0.1 atm). Liquid chromatography-tandem mass spectrometry (LC-MS/MS) was used to analyze the labeling pattern of amino-acids derived from the energy-module versus those that originate from the CBB-module (Methods). As shown in FIG. 2D, amino-acids derived from the CBB-module were almost fully labeled (e.g., serine and histidine), while amino-acids derived from the energy-module were mostly unlabeled (e.g., valine and threonine). Small deviations from complete labeling or no labeling are expected due to the release of unlabeled $CO_2$ from the TCA cycle and usage of labeled inorganic carbon in anaplerotic reactions respectively. The labeling pattern was verified in a reciprocal experiment where the bacteria was cultivated on uniformly labeled $^{13}$pyruvate and non-labeled $CO_2$. In this experiment serine and histidine were not labeled, while valine and threonine were almost fully labeled (FIG. 12). In addition, the labeling of intracellular precursor metabolites in the CBB and energy modules were analyzed, and as in the case of amino-acids, the labeling pattern matched the expected outcome from $CO_2$ fixation by the CBB module (FIGS. 13A-C). Semiautotrophic phenotypes of clones isolated from all three chemostats were similarly validated using labeling experiments (FIGS. 12 and 13A-C). Finally, isotopic analysis of biomass content revealed that ≈35% of cellular carbon originated from inorganic $CO_2$ (FIG. 2E), matching the known fraction of biomass produced from CBB module metabolites[15] (FIG. 8). Therefore, it may be concluded that inorganic carbon fixation is entirely responsible for producing key biomass precursors.

To characterize the evolutionary process that led to the emergence of semiautotrophic growth, the experiment was repeated (FIG. 11B) and whole-population samples were sequenced across 12 time points at a temporal resolution of ≈2 weeks. In addition, clones displaying the semiautotrophic phenotype were isolated and sequenced. The temporal trajectories of mutations (FIG. 3A) were used to construct a Muller diagram[19,20] describing the clonal dynamics of the evolving population (FIG. 3B, Methods). Each sector in the diagram is a genotype, and a nested sector shares the mutations of its ancestor sector. During the first two months, four rapid nested mutational sweeps were observed (FIG. 3B, blue shaded sectors Tables 2 and 3) that led to fixation of mutations in the coding sequence of xylE (R160S in the low affinity transporter of D-xylose), topA (R168C in DNA topoisomerase), crp (K23NK insertion in transcriptional regulator of metabolic genes) and a short deletion in the promoter region of yjiY (carbon starvation associated protein, CstA homolog).

To identify the mutation which enabled the engineered strain to grow based on a fully functional non-native CBB cycle, three distinct clones which were isolated from the chemostat (~200 generations) and were able to grow on pyruvate only in the presence of $CO_2$ were isolated. The list of genetic mutations identified within the population samples from the chemostat experiment shown in FIGS. 3A-B are provided in Table 2. The list of genetic mutations identified in clones isolated from chemostat experiment shown in FIGS. 3A-B are provide in Table 3. The list of large chromosomal deletions in semiautotrophic clones isolated from the chemostat experiment shown in FIGS. 3A-B are provided in Table 4. Increased copy number of chromosomal sections in semiautotrophic clones isolated from chemostat experiment shown in FIGS. 3A-B are provided in Table 5. Mutations identified in population samples from the first chemostat experiment are provided in Table 6.

TABLE 2

| Gene | Name in FIG. 3: | Type (effect in protein) | Genomic change | Position relative to ORF start | Found in clones: | Genomic position | Related gene description |
|---|---|---|---|---|---|---|---|
| xylE | xylE | missense (R -> S) | G -> T | 478 | EV1-5 | 4,231,705 | D-xylose transporter |
| topA | topA | missense (R -> C) | C -> T | 502 | EV1-5 | 1,325,806 | DNA topoisomerase I, omega subunit |
| crp | cm | insertion (K -> NK) | +TAA | 69 | EV1-5 | 3,479,547 | cAMP-activated global transcription factor, mediator of catabolite repression |
| crp | crp* | insertion (K -> NIHK) | +CATTCATAA SEQ ID NO: 7 | 69 | None | 3,479,547 | cAMP-activated global transcription factor, mediator of catabolite repression |
| yjiY_p | yjiY | deletion | -GGT | -125 | EV1-5 | 4,581,222 | putative transporter (promoter region) |
| fliF | fliF | deletion (frameshift) | -C | 298 | EV4-5 | 2,007,007 | flagellar basal-body MS-ring and collar protein |
| mlc | mlc + ptsP | insertion (frameshift) | +AGAGAAA SEQ ID NO: 8 | 263 | EV1-3 | 1,662,559 | glucosamine anaerobic growth regulon transcriptional repressor; autorepressor |

TABLE 2-continued

| Gene | Name in FIG. 3: | Type (effect in protein) | Genomic change | Position relative to ORF start | Found in clones: | Genomic position | Related gene description |
|---|---|---|---|---|---|---|---|
| ptsP | mlc + ptsP | deletion (frameshift) | -CGACT SEQ ID NO: 9 | 24 | EV1-3 | 2,961,770 | fused PTS enzyme: PEP-protein phosphotransferase (enzyme I)/ GAF domain containing protein |
| rpoB | rpoB* | insertion (-> D) | +GAC | 598 | None | 4,171,770 | RNA polymerase, beta subunit |
| malK | malK + 2 | insertion (frameshift) | +CCGCCAGAA CGACGT GG TGTTGGTA SEQ ID NO: 10 | 1012 | EV1-3 | 4,237,723 | used maltose transport subunit, ATP-binding component of ABC superfamily/regulatory protein |
| thrA | malK + 2 | missense (G -> S) | G -> A | 1,207 | EV1-3 | 1,543 | Bifunctional aspartokinase/ homoserine dehydrogenase 1 |
| yfiH | malK + 2 | insertion (frameshift) | +C | 492 | EV1-3 | 2,727,902 | UPF0124 family protein |
| ptsI | ptsI* | insertion (N -> KVNRGN) | +AGTTAACC GTGGTAA SEQ ID NO: 11 | 1,401 | None | 2,528,825 | PEP-protein phosphotransferase of PTS system (enzyme I) |
| nadB_p | nadB* | deletion | -TTA | -76 | None | 2,703,703 | quinolinate synthase, L-aspartate oxidase (B protein) subunit (promoter region) |
| prs | prs + 4 | insertion (A-> ARVPITA) | +TCGTGTACC AATCACTGC SEQ ID NO: 12 | 330 | EV1-3 | 1,257,002 | Phosphoribosyl pyrophosphate synthase |
| nadR | prs + 4 | missense (A -> T) | G -> A | 904 | EV1-3 | 4,618,035 | trifunctional protein: nicotinamide mononucleotide adenylyltransferase, ribosylnieotinamide kinase, transcriptional repressor |
| brnQ | prs + 4 | deletion (frameshift) | -C | 396 | EV1-3 | 415,442 | branched-chain amino acid transport system 2 carrier protein; LIV-II transport system for Ile, Leu, and Val |
| tufA | prs + 4 | insertion (frameshift) | +A | 317 | EV1-3 | 3,464,372 | translation elongation factor EF-Tu 1 |
| ycbZ | prs + 4 | insertion (I -> IAN) | +TTGGCA SEQ ID NO: 13 | 219 | EV1-3 | 1,013,537 | putative peptidase |
| brnQ | brnQ* | deletion (frameshift) | -G | 1,073 | None | 416,119 | branched-chain amino acid transport system 2 carrier protein; LIV-II transport system for Ile, Leu, and Val |
| mlc | mlc' + malK' + prs' + 7 | insertion (D -> DQIN) | +TTATTTGAT SEQ ID NO: 14 | 32 | EV4-5 | 1,662,790 | glucosamine anaerobic growth regulon transcriptional repressor; autorepressor |

TABLE 2-continued

| Gene | Name in FIG. 3: | Type (effect in protein) | Genomic change | Position relative to ORF start | Found in clones: | Genomic position | Related gene description |
|---|---|---|---|---|---|---|---|
| prs | mlc' + malK' CH-prs' + 7 | insertion (T -> TDMAI) | +ATTGCCA TATCG SEQ ID NO: 15 | 561 | EV4-5 | 1,256,771 | Phosphoribosyl pyrophosphate synthase |
| malK | mlc'+ malK' + prs' + 7 | insertion (frameshift) | +GACGTGGT GTTGGTAGAAG SEQ ID NO: 16 | 1,016 | EV4-5 | 4,237,727 | fused maltose transport subunit, ATP-binding component of ABC superfamily/regulatory protein |
| slyA | mlc' + malK' + prs' + 7 | insertion (frameshift) | +ATTTC | 337 | EV4-5 | 1,314,745 | global transcriptional regulator |
| ppsR | mlc' + malK' + prs'+ 7 | insertion (frameshift) | +GT | 736 | EV4-5 | 1,782,437 | bifunctional regulatory protein: PEP synthase kinase and PEP synthase pyrophosphorylase |
| rpoC | mlc' + malK' + prs' + 7 | missense (G -> S) | G -> A | 2,026 | EV4-5 | 4,177,303 | RNA polymerase, beta prime subunit |
| rne | mlc' + malK' + prs' + 7 | insertion (-> RVRK) | +TTTACGC ACGCG SEQ ID NO: 17 | 1,462 | EV4-5 | 1,138,362 | fused ribonucleaseE: endoribonuclease/RNA-binding protein/RNA degradosome binding protein |
| ycjQ | mlc' + malK' + prs' + 7 | synonymous | G -> A | 84 | EV4-5 | 1,369,303 | putative Zn-dependent NAD(P)-binding oxidoreductase |
| hisL_p | mlc' + malK' + prs' + 7 | insertion | +TAT | -83 | EV4-5 | 2,083,394 | his operon leader peptide promoter region) |
| psuK_p | mlc' + malK' + prs' + 7 | insertion | +AA | -120 | EV4-5 | 2,252,896 | pseudouridine kinase (promoter region) |
| ebdA_p | cbdA | insertion | +GATAA | -62 | EV4-5 | 1,033,134 | cytochrome bd-II oxidase, subunit I (promoter region) |

TABLE 3

| Gene | Type (protein effect) | Genomic change | Position relative to ORF start | Found in clones: | Genomic position | Related gene description |
|---|---|---|---|---|---|---|
| malEp | insertion | +CACCTA SEQ ID NO: 18 | -48 | EV1-3 | 4,236,396 | maltose transporter subunit (promoter region) |
| opgH | nonsense (W -> stop) | G -> A | 2,007 | EV4 | 1,108,325 | membrane glycosyl transferase; nutrient-dependent cell size regulator, FtsZ assembly antagonist |
| pdhR | insertion (R -> HSRR) | +ATTCGC GTC SEQ ID NO: 19 | 575 | EV1 | 119,153 | pyruvate dehydrogcnase complex repressor; autorepressor |
| pyrH | Insertion (K -> IMGEK) | +TAATGGGTG AAA SEQ ID NO: 20 | 701 | EV1 | 189,042 | uridylate kinase |

TABLE 3-continued

| Gene | Type (protein effect) | Genomic change | Position relative to ORF start | Found in clones: | Genomic position | Related gene description |
|---|---|---|---|---|---|---|
| brnQ | insertion (truncation) | +TAAGA SEQ ID NO: 21 | 20 | EV1 | 415,066 | branched-chain amino acid transport system 2 carrier protein; LIV-II transport system for Ile, Leu, and Val |
| ybeL | insertion (frameshift) | +AATA | 117 | EV3 | 670,590 | DUF1451 family protein |
| dcm | insertion (frameshift) | +TTTTC SEQ ID NO: 22 | 558 | EV5 | 2,025,241 | DNA cytosine methyltransferase |
| asmA | insertion (frameshift) | +T | 530 | EV5 | 2,134,564 | suppressor of OmpF assembly mutants; putative outer membrane protein assembly factor; inner membrane-anchored periplasmic protein |
| yejM | insertion (frameshift) | +GATGCC GAGCG SEQ ID NO: 23 | 1,100 | EV1 | 2,278,954 | essential inner membrane DUF3413 domain-containing protein; lipid A production and membrane permeability factor |
| murP | insertion (frameshift) | +CTTTCAAT SEQ ID NO: 24 | 1,023 | EV2 | 2,541,054 | N-acetylmuramic acid permease, EIIBC component, PTS system |

TABLE 4

| Genes | Length [bp] | Found in clones: | start | end |
|---|---|---|---|---|
| mrp | 210 | EV4 | 2,186,581 | 2,186,791 |
| opgH, yceK, msyB, mdtG | 3,771 | EV1-3 | 1,106,931 | 1,110,702 |
| cryptic prophage e14 excision | 15,139 | EV4-5 | 1,191,728 | 1,206,867 |
| yhhJ, rbbA, yhiI, yhiJ, yhiL, yhiM, yhiN, pitA, uspB, uspA, dtpB, rsmJ, prlC, rlmJ, gor | 21,848 | EV2-3 | 3,618,291 | 3,640,139 |

TABLE 5

| Flanking genes | Length [bp] | Found in clones: | start | end |
|---|---|---|---|---|
| IS150 . . . xylAB xylFGH . . . rhsA | 83,646 | EV2-3 | 3,758,616 | 3,842,262 |
| rhsA . . . uhpB | 41,651 | EV2 | 3,713,998 | 3,755,649 |
| yqeH . . . ygeN | 8,928 | EV4 | 2,980,486 | 2,989,414 |
| tdcR, yhaB, yhaC | 1,999 | EV4 | 3,260,790 | 3,262,789 |
| yqiI, glgS | 1,601 | EV4 | 3,183,918 | 3,185,519 |

TABLE 6

| Gene | Type (effect in protein) | Genomic change | Position relative to ORF start | Detected in chemostat | Found in clones: | Genomic position | description |
|---|---|---|---|---|---|---|---|
| ydgC | deletion (frameshift) ( ) | -C | 157 | Yes | EV6-9 | 1,676,131 | inner membrane protein, GlpM family |
| topA | missense (R->P) | G->C | 104 | Yes | EV6-9 | 1,325,408 | DNA topoisomerase I, omega subunit |
| gatY_p | deletion | -T | -56 | Yes | EV6-9 | 2,170,739 | D-tagatose 1,6-bisphosphate aldolase 2, catalytic subunit |
| truB | deletion (frameshift) | -A | 593 | Yes | EV6-9 | 3,305,544 | tRNA pseudouridine(55) synthase |
| brnQ | deletion (frameshift) | -AT | 12 | Yes | EV6-9 | 415,058 | branched-chain amino acid transport system 2 carrier protein; LIV-II transport system for Ile, Leu, and Val |
| xylE | deletion (frameshift) | -T | 137 | Yes | EV6-9 | 4,232,046 | D-xylose transporter |
| yhdZ_reg | deletion | -A | +4 after stop (IG) | Yes | EV6-9 | 3,416,557 | putative amino-acid transporter subunit |

TABLE 6-continued

| Gene | Type (effect in protein) | Genomic change | Position relative to ORF start | Detected in chemostat | Found in clones: | Genomic position | description |
|---|---|---|---|---|---|---|---|
| malQ | deletion (frameshift) | -G | 1269 | Yes | EV6-9 | 3,542,161 | 4-alpha-glucanotransferase (amylomaltase) |
| xylF_P | deletion | -A | -69 | Yes | EV6-9 | 3,742,422 | D-xylose transporter subunit |
| nanC_Reg | SNP (transversion) | G->T | -594 (IG) | Yes | EV6-9 | 4,529,912 | N-acetylnuraminic acid outer membrane channel protein |
| yjiY_P | deletion | -TAA | -126 | Yes | EV6-9 | 4,581,222 | putative inner membrane protein |
| yciV | deletion (freamshift) | -C | 149 | Yes | EV6-9 | 1,317,625 | hypothetical protein |
| ppsR | deletion (freamshift) | -C | 184 | Yes | EV6-9 | 1,781,885 | bifunctional regulatory protein: PEP synthase kinase and PEP synthase pyrophosphorylase |
| prs | missense (A->T) | C->T | 283 | Yes | EV6-9 | 1,257,049 | phosphoribosylpyrophosphate synthase |
| dcm | deletion (freamshift) | -TGTA | 1102 | Yes | EV6-9 | 2,024,694 | DNA cytosine methyltransferase |
| slyA | deletion (-V) | -GTT | 322 | Yes | EV6-9 | 1,714,758 | DNA-binding transcriptional activator |
| trmA | deletion (frameshift) | -AT | 1067 | Yes | EV6-9 | 4,152,131 | tRNA m(5)U54 methyltransferase, SAM-dependent |
| yjiY_P | deletion | -GGTAA SEQ ID NO: 25 | -123 | Yes | ? | 4,581,219 | putative inner membrane protein |
| yciV | deletion (frameshift) | -A | 488 | Yes | None | 1,317,964 | hypothetical protein |
| yehX | deletion (frameshift) | -CA | 830 | Yes | None | 2,210,056 | putative transporter subunit: ATP-binding component of ABC superfamily |
| pepA | deletion (-I) | -ATC | 549 | Yes | None | 4,475,218 | multifunctional aminopeptidase A: a cyteinylglycinase, transcription regulator and site-specific recombination factor |
| aroK | deletion | -A | -355 (IG) | No | EV6-9 | 3,512,778 | shikimate kinase I |
| ydbA_2 | delteion (frameshift) | -AT | 552 | No | EV7-9 | 1,465,324 | pseudogene, autotransporter homolog; interrupted by IS2 and IS30 |
| lptG_reg | | | | No | ? | | lipopolysaccharide export ABC permease of the LptBFGC export complex |
| cyoB | deletion (frameshift) | -A | 1006 | No | EV6 | 445,092 | cytochrome o ubiquinol oxidase subunit I |
| xylF_p | deletion | -A | -17 | No | EV6 | 3,724,474 | D-xylose transporter subunit |
| rimI | deletion (-M) | -ATT | 52 | No | EV6 | 4,598,053 | ribosomal-protein-S18-alanine N-acetyltransferase |
| pitA | deletion (frameshift) | -A | 957 | No | EV6 | 3,631,958 | phosphate transporter, low-affinity; tellurite importer |

TABLE 6-continued

| Gene | Type (effect in protein) | Genomic change | Position relative to ORF start | Detected in chemostat | Found in clones: | Genomic position | description |
|---|---|---|---|---|---|---|---|
| gltA_reg | deletion | -T | -299 (IG) | No | EV6 | 750,224 | citrate synthase |
| chbB | deletion (frameshift) | -A | 88 | No | EV6 | 1,815,789 | N,N'-diacetylchitobiose-specific enzyme IIB component of PTS |
| opgH | deletion (frameshift) | -TT | 1813 | No | EV6 | 1,108,131 | membrane glycosyltransierase; nutrient-dependent cell size regulator, FtsZ assembly antagonist |
| sdaC_reg | deletion | -CAT | -388 (IG) | No | EV6 | 2,921,202 | putative serine transporter |
| yqic_p | deletion | -AA | -36 | No | EV6 | 3,178,162 | BMFP family putative fusogenic protein |
| asmA | deletion (frameshift) | -T | 1066 | No | EV6 | 2,134,028 | putative assembly protein |
| xylA_reg | deletion | -AT | -139 (IG) | No | EV6 | 3,724,264 | D-xylose isomerase |
| ybaM | deletion (frameshift) | -T | 106 | No | EV6, EV8 | 485,622 | hypothetical protein |
| pyrH | deletion (-G) | -GTG | 695 | No | EV7-9 | 189,036 | uridvlate kinase |
| putP | deletion (frameshift) | -TC | 1304 | No | EV7, EV9 | 1,076,064 | proline:sodium symporter |
| queA | deletion (frameshift) | -TA | 177 | No | EV8 | 420,643 | S-adenosylmethionine:tRNA ribosyltransferase-isomerase |
| gadW_p | deletion | -TG | -51 | No | EV8 | 3,658,029 | transcriptional activator of gadA and gadBC; repressor of gadX |
| rpmH_reg | insertion | +TCACCCATG SEQ ID NO: 26 | -80 (IG) | No | EV8 | 3,877,616 | 50S ribosomal subunit protein L34 |
| sbp | deletion (frameshift) | -T | 294 | No | EV8 | 4,099,055 | sulfate transporter subunit |
| hflC | deletion (frameshift) ( ) | -AT | 977 | No | EV8 | 4,393,393 | modulator for HflB protease specific for phage lambda cII repressor |
| ldhA | insertion (I-> IHL) | +GGTGAA SEQ ID NO: 27 | 359 | No | EV8 | 1,436,743 | fermentative D-lactate dehydrogenase, NAD-dependent |
| sodB_p | deletion | -A | -19 | No | EV8 | 1,729,616 | superoxide dismutase, Fe |
| yciQ | deletion (frameshift) | -CT | 59 | No | EV8 | 1,319,060 | putative inner membrane protein |
| sdiA_reg | deletion | -A | -80 (IG) | No | EV8 | 1,990,393 | quorum-sensing transcriptional activator |
| adhE | deletion (frameshift) | -T | 426 | No | EV8 | 1,293,152 | fused acetaldehyde-CoA dehydrogenase/iron-dependent alcohol dehydrogenase/pyruvate-formate lyase deactivase |
| rseB | deletion (frameshift) | -T | 385 | No | EV8 | 2,701,729 | anti-sigma E factor, binds RseA |

TABLE 6-continued

| Gene | Type (effect in protein) | Genomic change | Position relative to ORF start | Detected in chemostat | Found in clones: | Genomic position | description |
|---|---|---|---|---|---|---|---|
| yheS_p | deletion | -CAT | -44 | No | EV8 | 3,474,602 | putative transporter subunit of ABC superfamily:ATP-binding component |
| nadR | deletion (frameshift) | -T | 249 | No | EV8 | 4,617,380 | trifunctional protein: nicotinamide mononucleotide adenylyltransferase, ribosylnicotinamide kinase, transcriptional repressor |
| glgB | deletion (frameshift) | -C | 396 | No | EV9 | 3,566,467 | 1,4-alpha-glucan branching enzyme |
| hrpA | deletion (frameshift) | -T | 1764 | No | EV9 | 1,479,081 | putative ATP-dependent helicase |
| pldA | deletion (frameshift) | -GA | 253 | No | EV9 | 3,998,474 | outer membrane phospholipase A |
| yaiL | deletion (frameshift) | -CA | 447 | No | EV9 | 372,674 | DUF2058 family protein |
| hflX | deletion (frameshift) | -G | 541 | No | EV9 | 4,391,029 | GTPase, stimulated by 50S subunit binding |
| yjiL | delteion (frameshift) | -T | 282 | No | EV9 | 4,554,225 | putative ATPase, activator of (R)-hydroxyglutaryl-CoA dehydratase |
| thiB | deletion (frameshift) | -TA | 463 | No | EV9 | 71,504 | thiamin transporter subunit |
| ybjC | deletion (frameshift) | -T | 15 | No | EV9 | 886,383 | conserved protein, DUF1418 family |
| nlpI | deletion (frameshift) | -AT | 417 | No | EV9 | 3,301,866 | lipoprotein involved in osmotic sensitivity and ftlamentation |
| clpA | deletion (frameshift) | -T | 415 | No | EV9 | 919,134 | ATPase and specificity subunit of ClpA-ClpP ATP-dependent serine protease, chaperone activity |
| clpA | deletion (frameshift) | -TC | 417 | No | EV9 | 919,136 | ATPase and specificity subunit of ClpA-ClpP ATP-dependent serine protease, chaperone activity |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Bassham, J. A. et al. The Path of Carbon in Photosynthesis. XXI. The Cyclic Regeneration of Carbon Dioxide Acceptor. J. Am. Chem. Soc. 76, 1760-1770 (1954).
2. Long, S. P., Marshall-Colon, A. & Zhu, X.-G. Meeting the Global Food Demand of the Future by Engineering Crop Photosynthesis and Yield Potential. Cell 161, 56-66 (2015).
3. Raines, C. A. The Calvin cycle revisited. Photosynth. Res. 75, 1-10 (2003).

4. Gronenberg, L. S., Marcheschi, R. J. & Liao, J. C. Next generation biofuel engineering in prokaryotes. Curr. Opin. Chem. Biol. 17, 462-471 (2013).
5. Church, G. M., Elowitz, M. B., Smolke, C. D., Voigt, C. A. & Weiss, R. Realizing the potential of synthetic biology. Nat. Rev. Mol. Cell Biol. 15, 289-294 (2014).
6. Raven, J. A., MacIntyre, H., Berman, T., Frank, I. B. & Others. Contributions of anoxygenic and oxygenic phototrophy and chemolithotrophy to carbon and oxygen fluxes in aquatic environments. in Aquatic Microbial Ecology 56, 177-192 (2009).
7. Parikh, M. R., Greene, D. N., Woods, K. K. & Matsumura, I. Directed evolution of RuBisCO hypermorphs through genetic selection in engineered *E. coli*. Protein Eng. Des. Sel. 19, 113-119 (2006).
8. Mueller-Cajar, O. & Whitney, S. M. Evolving improved *Synechococcus* Rubisco functional expression in *Escherichia coli*. Biochem. J 414, 205 (2008).
9. Somerville, C. R. & Somerville, S. C. Cloning and expression of the *Rhodospirillum rubrum* ribulosebisphosphate carboxylase gene in *E. Coli*. Mol. Gen. Genet. 193, 214-219, (1984).
10. Durao, P. et al. Opposing effects of folding and assembly chaperones on evolvability of Rubisco. Nat. Chem. Biol. 11, 148-155 (2015).
11. Schada von Borzyskowski, L., Rosenthal, R. G. & Erb, T. J. Evolutionary history and biotechnological future of carboxylases. J. Biotechnol. 168, 243-251 (2013).
12. Wang, D., Zhang, Y., Pohlmann, E. L. & Li, J. The poor growth of *Rhodospirillum rubrum* mutants lacking RubisCO is due to the accumulation of ribulose-1, 5-bisphosphate. Journal of (2011).
13. Hudson, G. S., Morell, M. K., Arvidsson, Y. & Andrews, T. J. Synthesis of spinach phosphoribulokinase and ribulose 1, 5-bisphosphate in *Escherichia coli*. Funct. Plant Biol. 19, 213-221 (1992).
14. Noor, E., Eden, E., Milo, R. & Alon, U. Central carbon metabolism as a minimal biochemical walk between precursors for biomass and energy. Mol. Cell 39, 809-820 (2010).
15. Neidhardt, F. C. et al. *Escherichia coli* and *Salmonella typhimurium*. Cellular and molecular biology. Volumes I and II. (American Society for Microbiology, 1987).
16. Sauer, U. Evolutionary engineering of industrially important microbial phenotypes.
Adv. Biochem. Eng. Biotechnol. 73, 129-169 (2001).
17. Sonderegger, M. & Sauer, U. Evolutionary engineering of *Saccharomyces cerevisiae* for anaerobic growth on xylose. Appl. Environ. Microbiol. 69, 1990-1998 (2003).
18. Feuer, R. et al. Model-based analysis of an adaptive evolution experiment with *Escherichia coli* in a pyruvate limited continuous culture with glycerol. EURASIP J. Bioinform. Syst. Biol. 2012, 14 (2012).
19. Elena, S. F. & Lenski, R. E. Evolution experiments with microorganisms: the dynamics and genetic bases of adaptation. Nat. Rev. Genet. 4, 457-469 (2003).
20. Lang, G. I. et al. Pervasive genetic hitchhiking and clonal interference in forty evolving yeast populations. Nature 500, 571-574 (2013).
21. Crozat, E., Philippe, N., Lenski, R. E., Geiselmann, J. & Schneider, D. Long-term experimental evolution in *Escherichia coli*. XII. DNA topology as a key target of selection. Genetics 169, 523-532 (2005).
22. Brown, C. J., Todd, K. M. & Rosenzweig, R. F. Multiple duplications of yeast hexose transport genes in response to selection in a glucose-limited environment. Mol. Biol. Evol. 15, 931-942 (1998).
23. Desai, M. M. & Fisher, D. S. Beneficial Mutation-Selection Balance and the Effect of Linkage on Positive Selection. Genetics 176, 1759-1798 (2007).
24. Baba, T., Ara, T., Hasegawa, M. & Takai, Y. Construction of *Escherichia coli* K-12 in-frame, single-gene knockout mutants: the Keio collection. Mol. Syst. Biol. (2006).
25. Lennox, E. S. Transduction of linked genetic characters of the host by bacteriophage P1. Virology 1, 190-206 (1955).
26. Datsenko, K. A. & Wanner, B. L. One-step inactivation of chromosomal genes in *Escherichia coli* K-12 using PCR products. Proc. Natl. Acad. Sci. U.S.A 97, 6640-6645 (2000).
27. Zelcbuch, L. et al. Spanning high-dimensional expression space using ribosome-binding site combinatorics. Nucleic Acids Res. 41, e98 (2013).
28. Orth, J. D., Thiele, I. & Palsson, B. Ø. What is flux balance analysis? Nat. Biotechnol. 28, 245-248 (2010).
29. Reznik, E., Mehta, P. & Segre, D. Flux imbalance analysis and the sensitivity of cellular growth to changes in metabolite pools. PLoS Comput. Biol. 9, e1003195 (2013).
30. Ebrahim, A., Lerman, J. A., Palsson, B. O. & Hyduke, D. R. COBRApy: COnstraints-Based Reconstruction and Analysis for Python. BMC Syst. Biol. 7, 74 (2013).
31. Burgard, A. P., Pharkya, P. & Maranas, C. D. Optknock: a bilevel programming framework for identifying gene knockout strategies for microbial strain optimization.
Biotechnol. Bioeng. 84, 647-657 (2003).
32. Xu, Z., Zheng, P., Sun, J. & Ma, Y. ReacKnock: identifying reaction deletion strategies for microbial strain optimization based on genome-scale metabolic network. PLoS One 8, e72150 (2013).
33. Tepper, N. & Shlomi, T. Predicting metabolic engineering knockout strategies for chemical production: accounting for competing pathways. Bioinformatics 26, 536-543 (2010).
34. Tepper, N. & Shlomi, T. Computational design of auxotrophy-dependent microbial biosensors for combinatorial metabolic engineering experiments. PLoS One 6, e16274 (2011).
35. Blecher-Gonen, R. et al. High-throughput chromatin immunoprecipitation for genome-wide mapping of in vivo protein-DNA interactions and epigenomic states. Nat. Protoc. 8, 539-554 (2013).
36. Grenier, F., Matteau, D., Baby, V. & Rodrigue, S. Complete Genome Sequence of *Escherichia coli* BW25113. Genome Announc. 2, (2014).
37. Li, H. & Durbin, R. Fast and accurate short read alignment with Burrows-Wheeler transform. Bioinformatics (2009).
38. McKenna, A. et al. The Genome Analysis Toolkit: a MapReduce framework for analyzing next-generation DNA sequencing data. Genome Res. 20, 1297-1303 (2010).
39. Kearse, M. et al. Geneious Basic: an integrated and extendable desktop software platform for the organization and analysis of sequence data. Bioinformatics 28, 1647-1649 (2012).

What is claimed is:

1. An *E. coli* which is genetically modified to express phosphoribulokinase (prk) and Ribulose-Bisphosphate Carboxylase (RuBisCo), wherein said *E. coli* produces a first essential biomass precursor by metabolizing $CO_2$, wherein the *E. coli* produces a second biomass precursor by metabolizing an organic carbon source and not by metabolizing $CO_2$, wherein the *E. coli* does not use said organic carbon source for producing said first essential biomass precursor, wherein said *E. Coli* is further modified so as to downregulate expression or activity of phosphoglycerate mutase (gpm).

2. The microorganism of claim 1, which generates ATP and NADH by metabolizing said organic carbon source.

3. The microorganism of claim 1, wherein said first essential biomass precursor is derived solely from $CO_2$.

4. The microorganism of claim 1, wherein said first essential biomass precursor is derived from $CO_2$ and a second organic carbon source.

5. The microorganism of claim 1, wherein said *E. Coli* is further modified so as to down-regulate expression or activity of phosphofructokinase (pfk) or ribose-5-phosphate isomerase (rpi).

6. The microorganism of claim 1, wherein said *E. Coli* has a deletion in a gene selected from the group consisting of glucose 6-phosphate-1-dehydrogenase (zwf) 6-phosphogluconate dehydratase (edd) and ketohydroxyglutarate aldolase (eda), malate synthase A (aceB), isocitrate lyase (aceA) and isocitrate dehydrogenase kinase/phosphatase (aceK).

7. A cell culture comprising the microorganism of claim 1 and a medium comprising an organic carbon source.

8. A genetically modified *E. Coli* which expresses a recombinant phosphoribulokinase (prk) and Ribulose-Bisphosphate Carboxylase (RuBisCo) wherein the genes zwf is knocked-out or downregulated.

9. The genetically modified *E. Coli* of claim 8, being an autotroph.

10. The genetically modified *E. Coli* of claim 8, wherein the gene aceBAK and malate synthase G (glcB) are knocked-out or downregulated.

11. The genetically modified *E. Coli* of claim 8, wherein the genes aceBAK, malate synthase G (glcB), phosphoenolpyruvate synthase (pps) and phosphoenolpyruvate carboxykinase (pck) are knocked-out or downregulated.

12. The genetically modified *E. Coli* of claim 8, wherein the genes aceBAK and phosphopyruvate hydratase (eno) are knocked-out or downregulated.

13. The genetically modified *E. Coli* of claim 8, wherein at least one gene selected from the group consisting of prs, yciV, topA, ydgC, slyA, dcm, malQ, brnQ, ppsR, truB, xylE and trmA is knocked-out or downregulated.

14. The genetically modified *E. Coli* of claim 8, having at least one mutation as set forth in Tables 2-6.

15. The genetically modified *E. Coli* of claim 8, wherein the gene pfkA, gpmA, gpmB and pfkB are knocked-out or down-regulated.

16. A cell culture comprising the genetically modified *E. Coli* of claim 8 and a medium comprising an organic carbon source.

* * * * *

SEQUENCE LISTING

<160> NUMBER OF SEQ ID NOS: 27

<210> SEQ ID NO 1
<211> LENGTH: 1422
<212> TYPE: DNA
<213> ORGANISM: Rhodospirillum rubrum

<400> SEQUENCE: 1

```
atgcatcatc accatcacca catggaccag tcatctcgtt acgtcaatct ggcgctcaag      60
gaagaggatc tgatcgccgg cggcgagcat gtgctttgtg cctatatcat gaagcccaag     120
gccggatatg gctatgtggc gaccgcggcg catttcgccg ccgagagttc gacgggcacc     180
aacgtcgagg tctgcaccac cgacgatttc acccggggcg tcgacgccct ggtctatgag     240
gtggacgagg cccgcgagct gaccaagatc gcctatccgg tggctttgtt cgaccgcaac     300
atcaccgacg gcaaggcgat gatcgcctcg ttcctgacgc tcaccatggg aaacaaccag     360
ggtatgggcg acgtggaata cgccaagatg cacgatttct atgtgcccga ggcttatcgc     420
gccctgtttg atggcccgag cgtcaatatc tcggccctgt ggaaagtgct ggggcggccc     480
gaggtcgacg gcggtctggt cgtcggcacg atcatcaagc cgaagctcgg cctgcgtccc     540
aagcccttcg ccgaggcctg ccacgccttc tggctgggcg cgacttcat caagaacgac      600 gagccccagg gcaatcagcc cttcgcccCC ttgcgcgaca ccatcgccct ggtcgccgac     660
gccatgaggc gggcccagga cgagaccggc gaggccaagc tgttctcggc caatatcacc     720
gccgacgatc ccttcgagat catcgcccgt ggcgagtatg tgctggagac cttcggcgag     780
aacgcctcgc atgtcgcctt gctggtcgac ggctatgtcg ccggcgccgc ggcgatcacc     840
acggcgcgcc gccgcttccc cgataacttc ttgcattatc accgggctgg ccacggcgcc     900
gtcacctcgc cccagtccaa gcgcggctat accgccttcg tccattgcaa gatggcccgc     960
cttcaaggcg ccagcggcat ccacaccggc catgggct ttggcaagat ggaaggcgag      1020
tccagcgacc gcgccatcgc ctatatgctg acccaggacg aggcccaggg gccgttctac    1080
cgtcaatcct ggggcggcat gaaggcttgt acgccgatca tcagcggcgg catgaacgcc    1140
ctgcgcatgc ccggcttctt cgagaacctg ggtaatgcca atgtcatctt gaccgccggc    1200
ggcggcgcct tcggccatat cgacggcccg gtggccgggg cgcggtcgtt gcgtcaagcc    1260
tggcaagcct ggcgggacgg ggttccggtt ctggactatg cccgcgagca aaggaactg     1320 gcccgcgcct tcgagtcctt ccccggcgac gccgaccaga tctatccggg ctggcgcaag    1380
gccctgggcg tcgaggacac ccgcagcgcc cttccggcgt aa                       1422
```

<210> SEQ ID NO 2
<211> LENGTH: 1019
<212> TYPE: DNA
<213> ORGANISM: Synechococcus elongatus

<400> SEQUENCE: 2

```
tgcatcatca ccatcaccac agcaagccag atcgtgttgt tttgatcggc gttgccggtg      60
actccggttg cggcaaatca accttcctaa atcgccttgc cgacttgttt ggtacggaat     120
tgatgacggt catctgcttg gatgactatc acagtctcga tcgcaagggc cggaaggaag     180
caggcgtaac ggctttggat ccccgcgcca acaactttga cttgatgtat gaacaggtca     240
aggcgttgaa gaacggcgaa acgatcatga agccgatcta caaccatgaa accggcttga     300
tcgatccgcc cgaaaaaatc gaacccaatc gcatcattgt gatcgagggt ctgcatccgc     360
tttacgacga gcgcgtgcgt gaactgctcg atttcagcgt ttacctcgac atcgatgacg     420
```

```
aagtcaaaat cgcttggaag atccaacgcg atatggcaga acgcggccac tcctacgaag     480
atgtcctcgc ctcgatcgaa gcgcgccgcc ctgacttcaa ggcctacatt gagccccagc     540
gtggccatgc ggacatcgtc atccgcgtca tgccgaccca gctaatcccc aatgacaccg     600
agcgcaaggt gctgcgggtg cagttgatcc aacgggaagg ccgcgatggt tttgagccgg     660
cttacctgtt cgacgaaggt tcgaccatcc agtggacgcc ctgcggtcgt aagctgacct     720
gctcctatcc gggcattcgc ttagcctacg gccctgacac ctactacggt cacgaagtct     780
cagtgcttga ggtcgacggt cagttcgaga acctcgaaga gatgatctac gtcgagggcc     840
acctcagcaa gaccgacacg cagtactacg gtgagttgac ccacctgctg ctacagcaca     900
aagattaccc gggttcgaac aacggcacgg gtctgttcca agtgctgacc ggcctgaaaa     960
tgcgggcggc ctatgagcgt ttgacctccc aagcagcacc cgtcgccgct agtgtctag    1019

<210> SEQ ID NO 3
<211> LENGTH: 660
<212> TYPE: DNA
<213> ORGANISM: Rhodospirillum rubrum

<400> SEQUENCE: 3
atgcatcatc accatcacca cgacatccag gatctcatta ccaacaatcg gaaatgggcc      60
gaggagcgcg aatccgccct tcctggctat tttcatatcc tcagcgaagt gcagtcgccg     120 aagttttttgt ggatcggctg ctcggactcg cgggtgccgg ccaatgaaat cgtcggcatg     180
cagccgggcg aacttttcgt tcaccgcaac atcgccaacg ttgttcccca tgccgacgcc     240
aattgccacg ccgtgctcga atacgccatc gacgtgctga aggtcgagca catcatggtc     300
gtcggccatt acggctgcgg cggggttcgc gccgccctga accgtctggc catggggccg     360
atcgacaact ggctgtccca catcaaggac atcgcccgta tcttcgccgc cgagctggaa     420
gacctacccg acgaggaaag ccgggtcgac cggctgtgcg aactcaacgc catggcccag     480
gtgatgaacg tggcgcgcac ctcgatggtt caggcggctt ggcgacgcgg ccagcctttg     540
gccatccacg cttggtgcta tggtctgaag actgggctgg tcaatgatct tggccgaacc     600
ctaacccgca tcgccgatct gcccgaaccc tatcggctga tctttcccga tcaggtctaa     660

<210> SEQ ID NO 4
<211> LENGTH: 466
<212> TYPE: PRT
<213> ORGANISM: Rhodospirillum rubrum

<400> SEQUENCE: 4

Met Asp Gln Ser Ser Arg Tyr Val Asn Leu Ala Leu Lys Glu Glu Asp
1               5                   10                  15

Leu Ile Ala Gly Gly Glu His Val Leu Cys Ala Tyr Ile Met Lys Pro
            20                  25                  30

Lys Ala Gly Tyr Gly Tyr Val Ala Thr Ala Ala His Phe Ala Ala Glu
        35                  40                  45

Ser Ser Thr Gly Thr Asn Val Glu Val Cys Thr Thr Asp Asp Phe Thr
    50                  55                  60

Arg Gly Val Asp Ala Leu Val Tyr Glu Val Asp Glu Ala Arg Glu Leu
65                  70                  75                  80

Thr Lys Ile Ala Tyr Pro Val Ala Leu Phe Asp Arg Asn Ile Thr Asp
                85                  90                  95

Gly Lys Ala Met Ile Ala Ser Phe Leu Thr Leu Thr Met Gly Asn Asn
            100                 105                 110
```

Gln Gly Met Gly Asp Val Glu Tyr Ala Lys Met His Asp Phe Tyr Val
            115                 120                 125

Pro Glu Ala Tyr Arg Ala Leu Phe Asp Gly Pro Ser Val Asn Ile Ser
        130                 135                 140

Ala Leu Trp Lys Val Leu Gly Arg Pro Glu Val Asp Gly Gly Leu Val
145                 150                 155                 160

Val Gly Thr Ile Ile Lys Pro Lys Leu Gly Leu Arg Pro Lys Pro Phe
                165                 170                 175

Ala Glu Ala Cys His Ala Phe Trp Leu Gly Asp Phe Ile Lys Asn
            180                 185                 190

Asp Glu Pro Gln Gly Asn Gln Pro Phe Ala Pro Leu Arg Asp Thr Ile
            195                 200                 205

Ala Leu Val Ala Asp Ala Met Arg Arg Ala Gln Asp Glu Thr Gly Glu
        210                 215                 220

Ala Lys Leu Phe Ser Ala Asn Ile Thr Ala Asp Pro Phe Glu Ile
225                 230                 235                 240

Ile Ala Arg Gly Glu Tyr Val Leu Glu Thr Phe Gly Glu Asn Ala Ser
                245                 250                 255

His Val Ala Leu Leu Val Asp Gly Tyr Val Ala Gly Ala Ala Ile
            260                 265                 270

Thr Thr Ala Arg Arg Phe Pro Asp Asn Phe Leu His Tyr His Arg
        275                 280                 285

Ala Gly His Gly Ala Val Thr Ser Pro Gln Ser Lys Arg Gly Tyr Thr
        290                 295                 300

Ala Phe Val His Cys Lys Met Ala Arg Leu Gln Gly Ala Ser Gly Ile
305                 310                 315                 320

His Thr Gly Thr Met Gly Phe Gly Lys Met Glu Gly Glu Ser Ser Asp
                325                 330                 335

Arg Ala Ile Ala Tyr Met Leu Thr Gln Asp Glu Ala Gln Gly Pro Phe
            340                 345                 350

Tyr Arg Gln Ser Trp Gly Gly Met Lys Ala Cys Thr Pro Ile Ile Ser
        355                 360                 365

Gly Gly Met Asn Ala Leu Arg Met Pro Gly Phe Phe Glu Asn Leu Gly
370                 375                 380

Asn Ala Asn Val Ile Leu Thr Ala Gly Gly Ala Phe Gly His Ile
385                 390                 395                 400

Asp Gly Pro Val Ala Gly Ala Arg Ser Leu Arg Gln Ala Trp Gln Ala
            405                 410                 415

Trp Arg Asp Gly Val Pro Val Leu Asp Tyr Ala Arg Glu His Lys Glu
            420                 425                 430

Leu Ala Arg Ala Phe Glu Ser Phe Pro Gly Asp Ala Asp Gln Ile Tyr
        435                 440                 445

Pro Gly Trp Arg Lys Ala Leu Gly Val Glu Asp Thr Arg Ser Ala Leu
450                 455                 460

Pro Ala
465

<210> SEQ ID NO 5
<211> LENGTH: 333
<212> TYPE: PRT
<213> ORGANISM: Synechococcus elongatus

<400> SEQUENCE: 5

Met Ser Lys Pro Asp Arg Val Val Leu Ile Gly Val Ala Gly Asp Ser

```
            1               5                  10                 15
          Gly Cys Gly Lys Ser Thr Phe Leu Asn Arg Leu Ala Asp Leu Phe Gly
                         20                 25                 30

Thr Glu Leu Met Thr Val Ile Cys Leu Asp Asp Tyr His Ser Leu Asp
                         35                 40                 45

Arg Lys Gly Arg Lys Glu Ala Gly Val Thr Ala Leu Asp Pro Arg Ala
                         50                 55                 60

Asn Asn Phe Asp Leu Met Tyr Glu Gln Val Lys Ala Leu Lys Asn Gly
           65                 70                 75                 80

Glu Thr Ile Met Lys Pro Ile Tyr Asn His Glu Thr Gly Leu Ile Asp
                         85                 90                 95

Pro Pro Glu Lys Ile Glu Pro Asn Arg Ile Ile Val Ile Glu Gly Leu
                        100                105                110

His Pro Leu Tyr Asp Glu Arg Val Arg Glu Leu Leu Asp Phe Ser Val
                        115                120                125

Tyr Leu Asp Ile Asp Asp Glu Val Lys Ile Ala Trp Lys Ile Gln Arg
                        130                135                140

Asp Met Ala Glu Arg Gly His Ser Tyr Glu Asp Val Leu Ala Ser Ile
          145                150                155                160

Glu Ala Arg Arg Pro Asp Phe Lys Ala Tyr Ile Glu Pro Gln Arg Gly
                        165                170                175

His Ala Asp Ile Val Ile Arg Val Met Pro Thr Gln Leu Ile Pro Asn
                        180                185                190

Asp Thr Glu Arg Lys Val Leu Arg Val Gln Leu Ile Gln Arg Glu Gly
                        195                200                205

Arg Asp Gly Phe Glu Pro Ala Tyr Leu Phe Asp Glu Gly Ser Thr Ile
                        210                215                220

Gln Trp Thr Pro Cys Gly Arg Lys Leu Thr Cys Ser Tyr Pro Gly Ile
          225                230                235                240

Arg Leu Ala Tyr Gly Pro Asp Thr Tyr Tyr Gly His Glu Val Ser Val
                        245                250                255

Leu Glu Val Asp Gly Gln Phe Glu Asn Leu Glu Glu Met Ile Tyr Val
                        260                265                270

Glu Gly His Leu Ser Lys Thr Asp Thr Gln Tyr Tyr Gly Glu Leu Thr
                        275                280                285

His Leu Leu Leu Gln His Lys Asp Tyr Pro Gly Ser Asn Asn Gly Thr
                        290                295                300

Gly Leu Phe Gln Val Leu Thr Gly Leu Lys Met Arg Ala Ala Tyr Glu
          305                310                315                320

Arg Leu Thr Ser Gln Ala Ala Pro Val Ala Ala Ser Val
                        325                330

<210> SEQ ID NO 6
<211> LENGTH: 213
<212> TYPE: PRT
<213> ORGANISM: Rhodospirillum rubrum

<400> SEQUENCE: 6

Met Asp Ile Gln Asp Leu Ile Thr Asn Asn Arg Lys Trp Ala Glu Glu
           1               5                  10                 15

Arg Glu Ser Ala Leu Pro Gly Tyr Phe His Ile Leu Ser Glu Val Gln
                         20                 25                 30

Ser Pro Lys Phe Leu Trp Ile Gly Cys Ser Asp Ser Arg Val Pro Ala
                         35                 40                 45
```

```
Asn Glu Ile Val Gly Met Gln Pro Gly Glu Leu Phe Val His Arg Asn
 50                  55                  60
Ile Ala Asn Val Val Pro His Ala Asp Ala Asn Cys His Ala Val Leu
 65                  70                  75                  80
Glu Tyr Ala Ile Asp Val Leu Lys Val Glu His Ile Met Val Val Gly
                 85                  90                  95
His Tyr Gly Cys Gly Val Arg Ala Ala Leu Asn Arg Leu Ala Met
            100                 105                 110
Gly Pro Ile Asp Asn Trp Leu Ser His Ile Lys Asp Ile Ala Arg Ile
        115                 120                 125
Phe Ala Ala Glu Leu Gly Asp Leu Pro Asp Glu Ser Arg Val Asp
130                 135                 140
Arg Leu Cys Glu Leu Asn Ala Met Ala Gln Val Met Asn Val Ala Arg
145                 150                 155                 160
Thr Ser Met Val Gln Ala Ala Trp Arg Arg Gly Gln Pro Leu Ala Ile
                165                 170                 175
His Ala Trp Cys Tyr Gly Leu Lys Thr Gly Leu Val Asn Asp Leu Gly
            180                 185                 190
Arg Thr Leu Thr Arg Ile Ala Asp Leu Pro Glu Pro Tyr Arg Leu Ile
        195                 200                 205
Phe Pro Asp Gln Val
        210

<210> SEQ ID NO 7
<211> LENGTH: 9
<212> TYPE: DNA
<213> ORGANISM: Artificial sequence
<220> FEATURE:
<223> OTHER INFORMATION: DNA insert

<400> SEQUENCE: 7 cattcataa                                                                 9

<210> SEQ ID NO 8
<211> LENGTH: 7
<212> TYPE: DNA
<213> ORGANISM: Artificial sequence
<220> FEATURE:
<223> OTHER INFORMATION: DNA insert

<400> SEQUENCE: 8 agagaaa                                                                   7

<210> SEQ ID NO 9
<211> LENGTH: 5
<212> TYPE: DNA
<213> ORGANISM: Artificial sequence
<220> FEATURE:
<223> OTHER INFORMATION: DNA deletion

<400> SEQUENCE: 9 cgact                                                                     5

<210> SEQ ID NO 10
<211> LENGTH: 25
<212> TYPE: DNA
<213> ORGANISM: Artificial sequence
<220> FEATURE:
<223> OTHER INFORMATION: DNA insert

<400> SEQUENCE: 10
```
ccgccagaac gacgtggtgt tggta                                              25

<210> SEQ ID NO 11
<211> LENGTH: 15
<212> TYPE: DNA
<213> ORGANISM: Artificial sequence
<220> FEATURE:
<223> OTHER INFORMATION: DNA insert

<400> SEQUENCE: 11
agttaaccgt ggtaa                                                         15

<210> SEQ ID NO 12
<211> LENGTH: 18
<212> TYPE: DNA
<213> ORGANISM: Artificial sequence
<220> FEATURE:
<223> OTHER INFORMATION: DNA insert

<400> SEQUENCE: 12
tcgtgtacca atcactgc                                                      18

<210> SEQ ID NO 13
<211> LENGTH: 6
<212> TYPE: DNA
<213> ORGANISM: Artificial sequence
<220> FEATURE:
<223> OTHER INFORMATION: DNA insert

<400> SEQUENCE: 13 ttggca                                                                    6

<210> SEQ ID NO 14
<211> LENGTH: 9
<212> TYPE: DNA
<213> ORGANISM: Artificial sequence
<220> FEATURE:
<223> OTHER INFORMATION: DNA insert

<400> SEQUENCE: 14 ttatttgat                                                                 9

<210> SEQ ID NO 15
<211> LENGTH: 12
<212> TYPE: DNA
<213> ORGANISM: Artificial sequence
<220> FEATURE:
<223> OTHER INFORMATION: DNA insert

<400> SEQUENCE: 15
attgccatat cg                                                            12

<210> SEQ ID NO 16
<211> LENGTH: 19
<212> TYPE: DNA
<213> ORGANISM: Artificial sequence
<220> FEATURE:
<223> OTHER INFORMATION: DNA insert

<400> SEQUENCE: 16
gacgtggtgt tggtagaag                                                     19

<210> SEQ ID NO 17
<211> LENGTH: 12
<212> TYPE: DNA
<213> ORGANISM: Artificial sequence

```
<220> FEATURE:
<223> OTHER INFORMATION: DNA insert

<400> SEQUENCE: 17
tttacgcacg cg                                                              12

<210> SEQ ID NO 18
<211> LENGTH: 6
<212> TYPE: DNA
<213> ORGANISM: Artificial sequence
<220> FEATURE:
<223> OTHER INFORMATION: DNA insert

<400> SEQUENCE: 18 caccta                                                                      6

<210> SEQ ID NO 19
<211> LENGTH: 9
<212> TYPE: DNA
<213> ORGANISM: Artificial sequence
<220> FEATURE:
<223> OTHER INFORMATION: DNA insert

<400> SEQUENCE: 19 attcgcgtc                                                                   9

<210> SEQ ID NO 20
<211> LENGTH: 12
<212> TYPE: DNA
<213> ORGANISM: Artificial sequence
<220> FEATURE:
<223> OTHER INFORMATION: DNA insert

<400> SEQUENCE: 20
taatgggtga aa                                                              12

<210> SEQ ID NO 21
<211> LENGTH: 5
<212> TYPE: DNA
<213> ORGANISM: Artificial sequence
<220> FEATURE:
<223> OTHER INFORMATION: DNA insert

<400> SEQUENCE: 21 taaga                                                                       5

<210> SEQ ID NO 22
<211> LENGTH: 5
<212> TYPE: DNA
<213> ORGANISM: Artificial sequence
<220> FEATURE:
<223> OTHER INFORMATION: DNA insert

<400> SEQUENCE: 22 ttttc                                                                       5

<210> SEQ ID NO 23
<211> LENGTH: 11
<212> TYPE: DNA
<213> ORGANISM: Artificial sequence
<220> FEATURE:
<223> OTHER INFORMATION: DNA insert

<400> SEQUENCE: 23
gatgccgagc g                                                               11
```

```
<210> SEQ ID NO 24
<211> LENGTH: 8
<212> TYPE: DNA
<213> ORGANISM: Artificial sequence
<220> FEATURE:
<223> OTHER INFORMATION: DNA insert

<400> SEQUENCE: 24 ctttcaat                                                                    8

<210> SEQ ID NO 25
<211> LENGTH: 5
<212> TYPE: DNA
<213> ORGANISM: Artificial sequence
<220> FEATURE:
<223> OTHER INFORMATION: DNA deletion

<400> SEQUENCE: 25 ggtaa                                                                       5

<210> SEQ ID NO 26
<211> LENGTH: 9
<212> TYPE: DNA
<213> ORGANISM: Artificial sequence
<220> FEATURE:
<223> OTHER INFORMATION: DNA insert

<400> SEQUENCE: 26 tcacccatg                                                                   9

<210> SEQ ID NO 27
<211> LENGTH: 6
<212> TYPE: DNA
<213> ORGANISM: Artificial sequence
<220> FEATURE:
<223> OTHER INFORMATION: DNA insert

<400> SEQUENCE: 27 ggtgaa                                                                      6
```